(12) United States Patent
Kawata et al.

(10) Patent No.: US 9,267,890 B2
(45) Date of Patent: Feb. 23, 2016

(54) NUCLEIC ACID ANALYZER

(75) Inventors: Eiji Kawata, Kisarazu (JP); Shuichi Akashi, Kisarazu (JP); Hiroyuki Kuroki, Kuki (JP)

(73) Assignee: TOPPAN PRINTING CO., LTD., Tokyo (JP)

(*) Notice: Subject to any disclaimer, the term of this patent is extended or adjusted under 35 U.S.C. 154(b) by 284 days.

(21) Appl. No.: 13/498,818

(22) PCT Filed: Sep. 30, 2010

(86) PCT No.: PCT/JP2010/067030
§ 371 (c)(1),
(2), (4) Date: Mar. 28, 2012

(87) PCT Pub. No.: WO2011/040504
PCT Pub. Date: Apr. 7, 2011

(65) Prior Publication Data
US 2012/0184025 A1    Jul. 19, 2012

(30) Foreign Application Priority Data

Sep. 30, 2009   (JP) ............................... P2009-228809

(51) Int. Cl.
*B01L 1/00*       (2006.01)
*B01L 3/00*       (2006.01)
(Continued)

(52) U.S. Cl.
CPC ............ *G01N 21/6452* (2013.01); *G01N 21/07* (2013.01); *G01N 35/00069* (2013.01); *G01N 2021/0325* (2013.01)

(58) Field of Classification Search
CPC ..... B01L 3/50; B01L 3/5027; B01L 2200/04; B01L 3/56; B01L 3/52; B01L 3/502715; B01L 2300/0861
See application file for complete search history.

(56) References Cited

U.S. PATENT DOCUMENTS 6,337,053 B1     1/2002  Tajima
2006/0091085 A1* 5/2006  Kobayashi et al. ........... 210/787
(Continued)

FOREIGN PATENT DOCUMENTS

CN    1965080    5/2007
JP    2-232563   9/1990
(Continued)

OTHER PUBLICATIONS

International Search Report mailed Nov. 22, 2010 issued in corresponding International Patent Application No. PCT/JP2010/067030.
(Continued)

*Primary Examiner* — Nathan Bowers

(57) ABSTRACT

A nucleic acid analyzer includes a nucleic acid purification kit yielding a nucleic acid solution by isolating and purifying nucleic acid from a specimen; a nucleic acid analysis chip having a rotation axis positioned at a center thereof, with reaction containers at an outer portion than the rotation axis, and feeding the acid to the containers through centrifugal force; a specimen-introducing part on which the kit is placed; an analysis chip holder at the specimen-introducing part and supporting the chip; a purification treatment unit injecting the nucleic acid solution containing the nucleic acid into the chip; a centrifugal liquid feed unit feeding the nucleic acid solution to the containers by rotating the chip about the rotation axis; an analysis unit analyzing reaction products in the containers; and a transport part transporting the specimen-introducing part to the purification treatment unit, the centrifugal liquid feed unit, and the analysis unit.

36 Claims, 18 Drawing Sheets

(51) Int. Cl.
    *G01N 21/64*     (2006.01)
    *G01N 21/07*     (2006.01)
    *G01N 35/00*     (2006.01)
    *G01N 21/03*     (2006.01)

(56) References Cited

U.S. PATENT DOCUMENTS

| | | | | |
|---|---|---|---|---|
| 2008/0253927 | A1* | 10/2008 | Burow et al. | 422/64 |
| 2008/0314895 | A1 | 12/2008 | Bedingham et al. | |
| 2009/0130745 | A1* | 5/2009 | Williams et al. | 435/287.2 |
| 2011/0303657 | A1* | 12/2011 | Bedingham et al. | 219/752 |
| 2013/0065256 | A1* | 3/2013 | Holtlund et al. | 435/7.92 |

FOREIGN PATENT DOCUMENTS

| | | |
|---|---|---|
| JP | 2003-310260 | 11/2003 |
| JP | 2005-62084 | 3/2005 |
| JP | 2005-192558 | 7/2005 |
| JP | 2005-204579 | 8/2005 |
| JP | 2005-257337 | 9/2005 |
| JP | 2005-537911 | 12/2005 |
| JP | 2006-126010 | 5/2006 |
| JP | 2007-330845 | 12/2007 |
| JP | 2009-22187 | 2/2009 |
| JP | 2009-41984 | 2/2009 |
| JP | 2009-97936 | 5/2009 |
| WO | 2005-118772 | 12/2005 |
| WO | 2005/118803 | 12/2005 |
| WO | WO 2006/054690 A1 | 5/2006 |
| WO | 2008/123019 | 10/2008 |
| WO | 2009/005001 | 1/2009 |

OTHER PUBLICATIONS

Japanese Office Action mailed Jan. 17, 2012 issued in corresponding Japanese Patent Application No. 2011-527917.
Japanese Office Action mailed Sep. 13, 2011 issued in corresponding Japanese Patent Application No. 2011-527917.
Office Action mailed Mar. 17, 2015 in corresponding Taiwanese Patent Application No. 099133014.
Japanese Office Action mailed Nov. 25, 2014 in corresponding Japanese Patent Application No. 2012-118973.
Japanese Office Action dated Jun. 30, 2015 in corresponding Japanese Patent Application No. 2012-118973.

* cited by examiner

NUCLEIC ACID ANALYZER

CROSS-REFERENCE TO RELATED APPLICATIONS

This application claims the benefit under 35 U.S.C. Section 371, of PCT International Application No. PCT/JP2010/067030, filed Sep. 30, 2010, which claimed priority to Japanese Application No. 2009-228809, filed Sep. 30, 2009 in the Japanese Patent Office, the disclosures of which are hereby incorporated by reference.

TECHNICAL FIELD

The present invention relates to a nucleic acid analyzer.

BACKGROUND ART

Single nucleotide polymorphisms (SNPs) are polymorphism that includes mutations at a single base within a DNA sequence formed of a plurality of bases. It has been known that differences in such nucleotide sequence cause personal differences in, for example, drug metabolism and the like.

Through the recent development of a gene test technique, nucleic acid is extracted from a specimen such as a biological sample taken from, for example, a patient, and differences in a gene such as SNPs are detected. The possibility is suggested that sensitivity to medicines can be predicted in advance by differences in genes. Accordingly, it is considered that a so-called tailor-made medical treatment (which is also referred to as order-made medical treatment) will be realized, which provides the optimum medical treatment (drug) for each patient while reducing the side effects of medicines.

A nucleic acid analyzer, which supplies a whole blood sample taken from a patient to a cartridge and purifies and analyzes nucleic acid using the cartridge, is disclosed in, for example, Patent Document 1 as a device that performs this gene test. According to the nucleic acid analyzer disclosed in Patent Document 1, it is possible to reduce a user's workload on the nucleic acid analysis by reducing the dependence on a user's manual work. In addition, it is possible to increase the reproducibility of the nucleic acid analysis without variations in the collection rate for nucleic acid that is caused by differences in the users' skill.

Further, a gene detection-determination device, which can measure a plurality of SNPs at one time by forming a plurality of reaction chambers used to measure a plurality of SNPs, is disclosed in Patent Document 2. According to this gene detection-determination device, it is possible to suppress the occurrence of human errors or contamination and to increase the accuracy of a gene test.

CITATION LIST

Patent Documents

[Patent Document 1] PCT International Publication No. WO2005-118772
[Patent Document 2] PCT International Publication No. WO2009-005001

SUMMARY OF INVENTION

Technical Problem

However, since one kind of reaction is performed using one cartridge in the nucleic acid analyzer disclosed in Patent Document 1, the kind of SNP which can be measured by one-time analysis is limited. For this reason, since it is necessary to supply the same specimens to a plurality of cartridges and to perform analysis several times in order to measure plural kinds of SNPs at one time, the work is troublesome. Further, since several disposable cartridges need to be used for the same specimen, there also is a problem in that the cost of expendable supplies is high when the nucleic acid analyzer is operated.

Moreover, in the gene detection-determination device disclosed in Patent Document 2, the purification of nucleic acid needs to be performed manually or by devices separate from the gene detection-determination device. Purified nucleic acid needs to be manually supplied to the gene detection-determination device by a user. For this reason, since operation is troublesome and purified nucleic acid is manually supplied, there is a possibility of variations occurring in test results due to measurement errors and the like.

The invention has been made in consideration of the above-mentioned circumstances, and an object of the invention is to provide a nucleic acid analyzer that can easily perform an accurate gene test.

Solution to Problem

The invention proposes the followings in order to achieve the object.

(1) A nucleic acid analyzer according to an aspect of the invention includes a nucleic acid purification kit that yields a nucleic acid solution by isolating and purifying nucleic acid from a specimen; a nucleic acid analysis chip that has a rotation axis positioned at a center thereof, includes a plurality of reaction containers at an outer portion than the rotation axis in a radial direction, and feeds the nucleic acid purified by the nucleic acid purification kit, to the reaction containers through centrifugal force around the rotation axis; a specimen-introducing part on which the nucleic acid purification kit is placed; an analysis chip holder that is provided at the specimen-introducing part and supports the nucleic acid analysis chip; a purification treatment unit that injects the nucleic acid solution containing the nucleic acid into the nucleic acid analysis chip; a centrifugal liquid feed unit that feeds the nucleic acid solution to each of the reaction containers by rotating the nucleic acid analysis chip about the rotation axis; an analysis unit that analyzes reaction products in the reaction containers; and transport part for relatively transporting the specimen-introducing part to each of the purification treatment unit, the centrifugal liquid feed unit, and the analysis unit.

(2) In the nucleic acid analyzer according to (1), the analysis unit may include a temperature control mechanism that comes into contact with an outer surface of the reaction containers of the nucleic acid analysis chip and heats or cools the reaction containers so that a temperature of the reaction containers follows a predetermined temperature change.

(3) In the nucleic acid analyzer according to (2), the analysis unit may include a fluorescence measuring section that emits excitation light having a predetermined wavelength that excites a fluorescent material in the reaction containers of the nucleic acid analysis chip, and measures an intensity of fluorescence emitted from the fluorescent material.

(4) In the nucleic acid analyzer according to any one of (1) to (3), the nucleic acid purification kit may include: oil that is supplied to the nucleic acid analysis chip; a dispensing chip-receiver in which at least an oil-dispensing chip that dispenses the oil is stored, and an oil-removing unit that removes surplus oil adhering to an outer surface of an end portion of the oil-dispensing chip.

(5) In the nucleic acid analyzer according to (4), the oil-removing unit may include a lipophilic wiper that comes into contact with the outer surface of the oil-dispensing chip when an end of the oil-dispensing chip is inserted.

(6) In the nucleic acid analyzer according to (4), the nucleic acid purification kit may include a box-shaped reagent cartridge, and a plurality of reagent-dispensing chips that are stored in the dispensing chip-receiver, and the reagent cartridge includes: a specimen storage portion that stores the specimen; an oil storage portion that stores the oil; a reagent storage portion that stores a liquid reagent used for the isolation and purification of the nucleic acid; a waste liquid storage portion that stores waste liquid generated during the isolation and the purification; and an extraction filter cartridge that purifies the nucleic acid of the specimen.

(7) In the nucleic acid analyzer according to (6), the reagent cartridge may be provided with an opening portion sealing film that seals each of the oil storage portion and the reagent storage portion and is formed penetrable by an end of the reagent-dispensing chip or the oil-dispensing chip.

(8) In the nucleic acid analyzer according to (6), the reagent cartridge may include a holding portion that detachably holds the extraction filter cartridge.

(9) In the nucleic acid analyzer according to (8), the holding portion may include an absorbent body that absorbs liquid passing through the extraction filter cartridge.

(10) The nucleic acid analyzer according to (6) may further include a cartridge-sealing film that seals an opening of the reagent cartridge.

(11) In the nucleic acid analyzer according to (6), the reagent cartridge may include a positioning mechanism that positions the reagent cartridge on the specimen-introducing part.

(12) In the nucleic acid analyzer according to (1), the nucleic acid analysis chip may include flow passages that are positioned closer to the rotation axis than the plurality of reaction containers and are connected to the plurality of reaction containers, and an injection port that is opened and formed closer to the rotation axis than the flow passages.

(13) In the nucleic acid analyzer according to (12), the injection port may be opened coaxially with the rotation axis. The nucleic acid analyzer may further include: a protruding wall portion that protrudes from the outer surface of the nucleic acid analysis chip so as to surround the injection port.

(14) In the nucleic acid analyzer according to (13), the protruding wall portion may have elasticity.

(15) In the nucleic acid analyzer according to (12), the flow passages may include main flow passages that are formed closer to the rotation axis than the reaction containers and communicate with the injection port, and a plurality of branch flow passages that are branched from the main flow passages, are connected to each of the reaction containers, and are formed so as to be thinner than the main flow passages.

(16) In the nucleic acid analyzer according to (12), the main flow passage may have a chevron shape that protrudes along the rotation axis.

(17) In the nucleic acid analyzer according to (12), at least a part of the reaction container may have optical transparency.

(18) In the nucleic acid analyzer according to (12), the nucleic acid analysis chip may include a chip body where concave portions forming the reaction containers and the flow passages are formed on one surface; and a lid body that is attached to the one surface of the chip body so as to lid the concave portions.

(19) In the nucleic acid analyzer according to (18), at least one of the chip body and the lid body may have optical transparency.

(20) In the nucleic acid analyzer according to (18), the chip body may be made of a resin material having optical transparency, and the lid body may be made of a metal material.

Advantageous Effects of Invention

According to the nucleic acid analyzer of the invention, since processes from the purification of nucleic acid to the analysis of nucleic acid can be automatically performed, it is possible to easily perform an accurate gene test.

DESCRIPTION OF EMBODIMENTS

A nucleic acid analyzer according to an embodiment of the invention will be described below.

Figure 1:
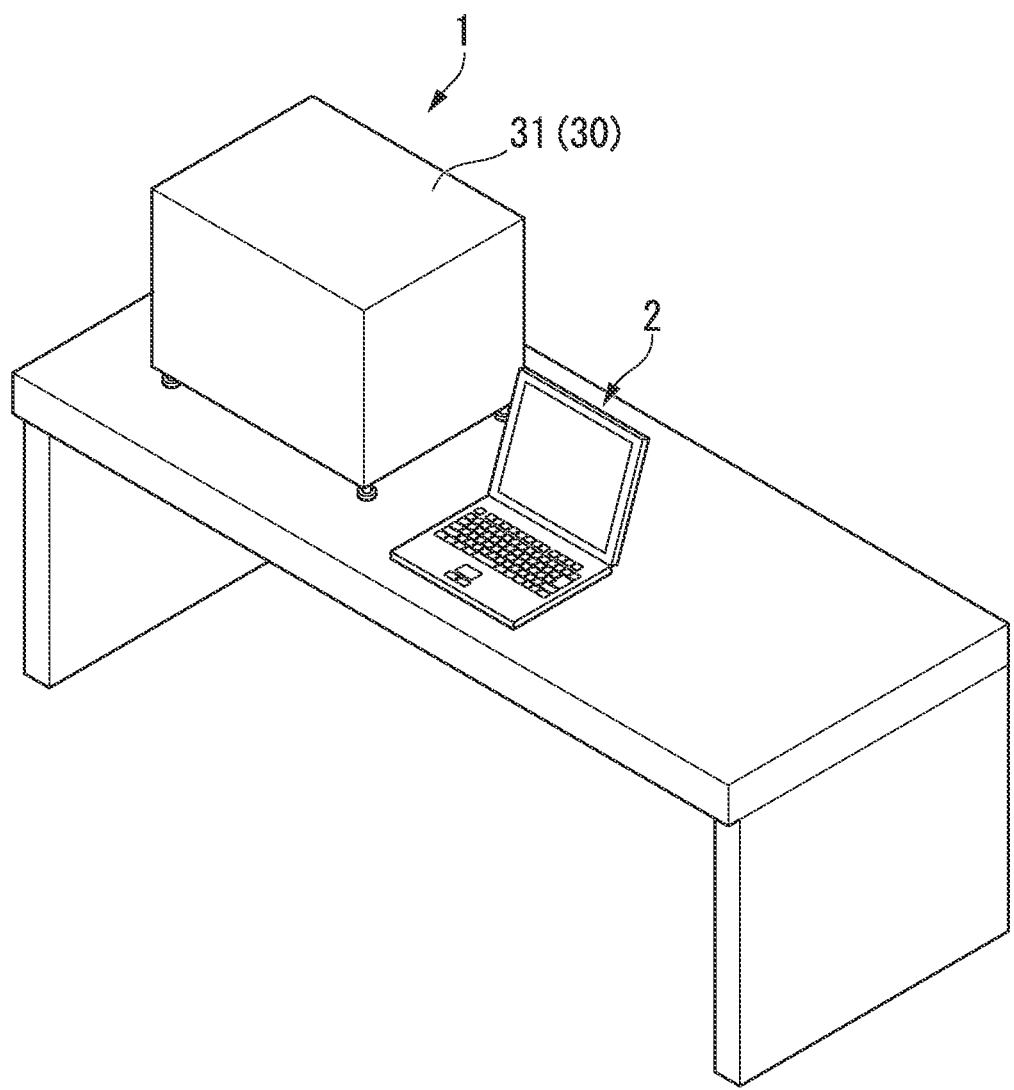
FIG. 1 is a perspective view showing the overview of a nucleic acid analyzer according to an embodiment of the invention.

First, the entire structure of a nucleic acid analyzer 1 according to this embodiment will be described with reference to FIGS. 1 and 2. FIG. 1 is a perspective view showing the appearance of the nucleic acid analyzer 1 according to this embodiment. Further, FIG. 2 is a plan view showing the structure of a part of the nucleic acid analyzer 1.

In this embodiment, the nucleic acid analyzer 1 automatically performs a series of operations that purify nucleic acid from a specimen, amplify a region of the purified nucleic acid including SNP (Single Nucleotide Polymorphisms) that is an object to be tested, and measure SNP of the amplified nucleic acid by the invader (registered trademark) method.

As shown in FIG. 1, the nucleic acid analyzer 1 is provided in, for example, a stationary housing 31. A terminal 2 is connected to the nucleic acid analyzer 1 through a signal line (not shown). The operation of a user can be input to the nucleic acid analyzer 1 by the terminal 2, or the results of the analysis of nucleic acid can be displayed on the terminal 2.

Figure 2:
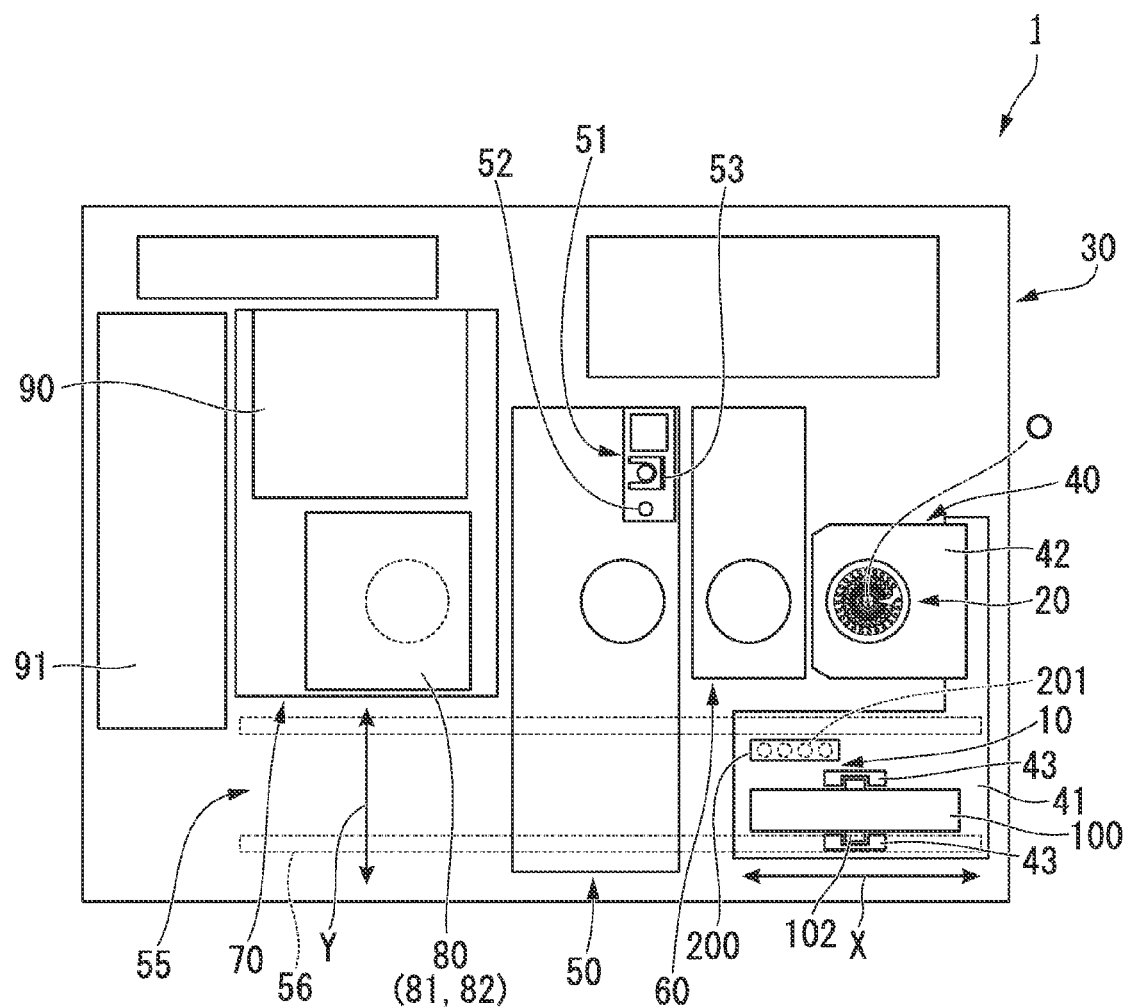
FIG. 2 is a plan view showing the structure of the nucleic acid analyzer.
Figure 8A:
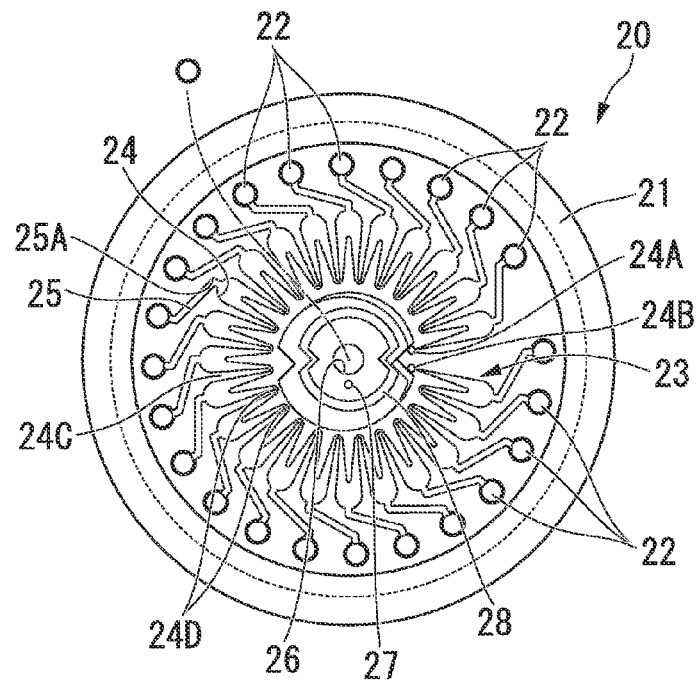
FIG. 8A is a plan view showing the structure of a nucleic acid analysis chip of the nucleic acid analyzer.

As shown in FIGS. 2 and 8A, the nucleic acid analyzer 1 includes a nucleic acid purification kit 10 that obtains a nucleic acid solution by isolating and purifying nucleic acid from a specimen; a nucleic acid analysis chip 20 that has a central axis (rotation axis) O positioned at the center thereof, includes a plurality of reaction containers 22 at the outer portion than the central axis O in a radial direction, and feeds the nucleic acid, which is purified by the nucleic acid purification kit 10, to the reaction containers 22 through centrifugal force around the central axis O; a specimen-introducing part 40 on which the nucleic acid purification kit 10 is placed; and an analyzer body 30.

Specifically, the nucleic acid purification kit 10 breaks down cells included in a specimen such as a biological sample, and isolates and purifies nucleic acid, which is included in the cells, by making the nucleic acid be adsorbed on a carrier. The nucleic acid analysis chip 20 performs a biochemical reaction on the nucleic acid that is purified by the nucleic acid purification kit 10.

Further, the nucleic acid purification kit 10 and the nucleic acid analysis chip 20 are disposed in the analyzer body 30, and the analyzer body performs a purification or analysis operation on the nucleic acid purification kit 10 and the nucleic acid analysis chip 20.

Specifically, as shown in FIG. 2, the analyzer body 30 includes an analysis chip holder 42 that is provided at the specimen-introducing part 40 and supports the nucleic acid analysis chip 20; a purification treatment unit 50 that isolates and purifies nucleic acid by the nucleic acid purification kit 10 and injects the nucleic acid solution containing the purified nucleic acid into the nucleic acid analysis chip 20; a centrifugal liquid feed unit 60 that feeds the nucleic acid solution to each of the reaction containers 22 by rotating the nucleic acid analysis chip 20 about the central axis O; an analysis unit 70 that analyzes reaction products in the reaction containers 22; and a transport unit (transport part) 55 that relatively transports the specimen-introducing part 40 to each of the purification treatment unit 50, the centrifugal liquid feed unit 60, and the analysis unit 70.

Figure 3:
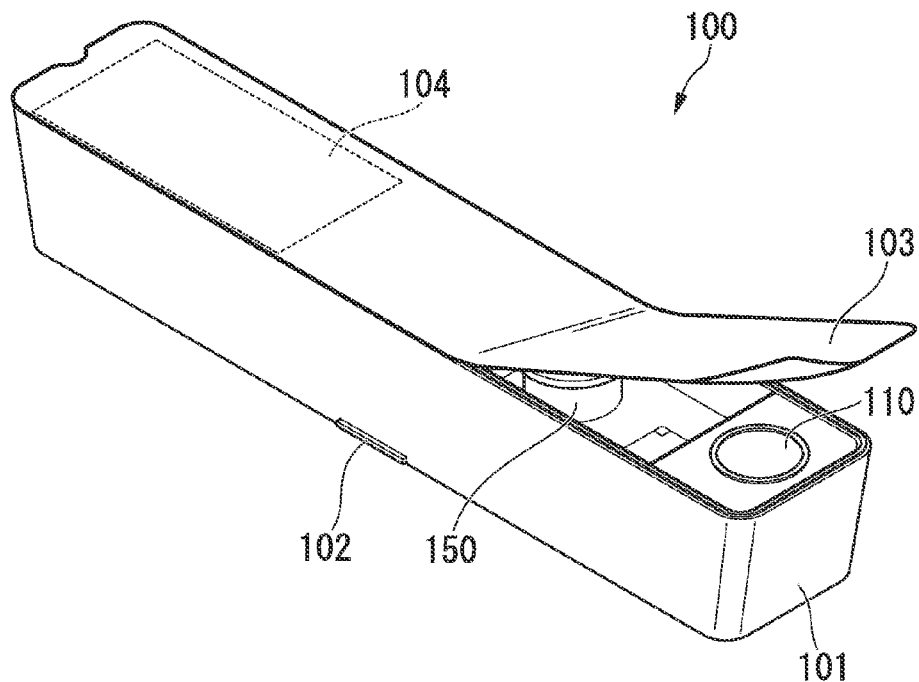
FIG. 3 is a perspective view showing the structure of a nucleic acid purification kit of the nucleic acid analyzer.
Figure 4:
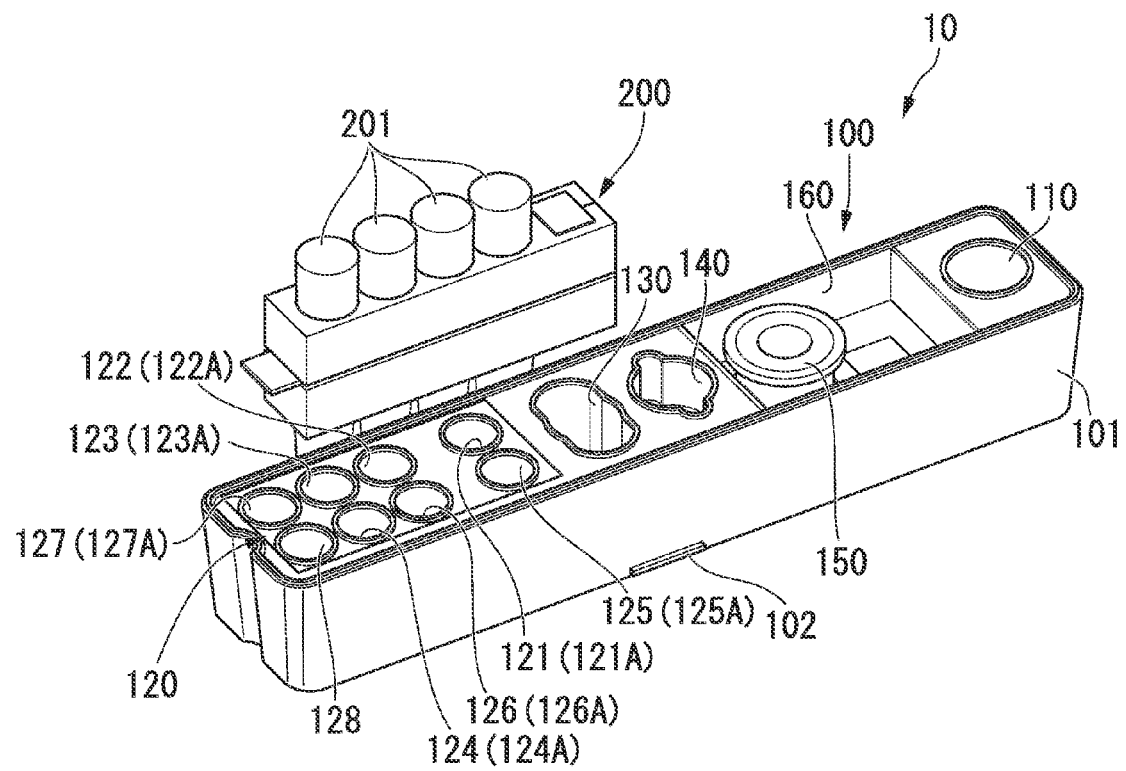
FIG. 4 is a perspective view showing the structure of the nucleic acid purification kit of the nucleic acid analyzer.
Figure 5:
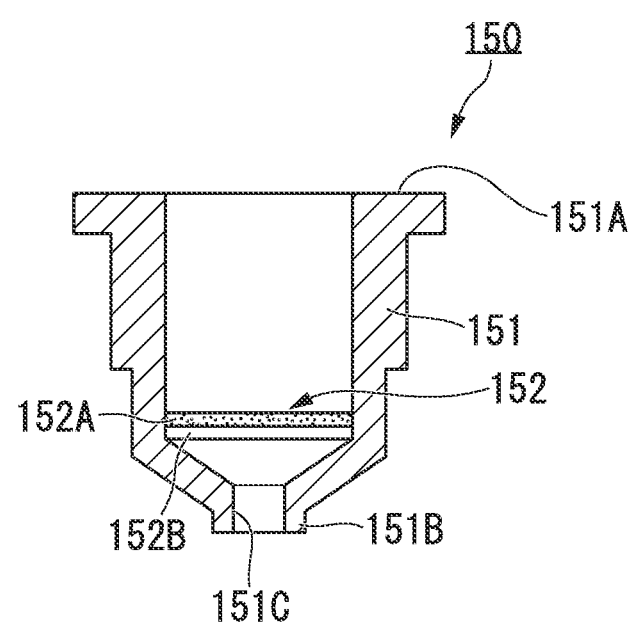
FIG. 5 is a cross-sectional view showing the structure of an extraction filter cartridge of the nucleic acid purification kit.
Figure 6A:
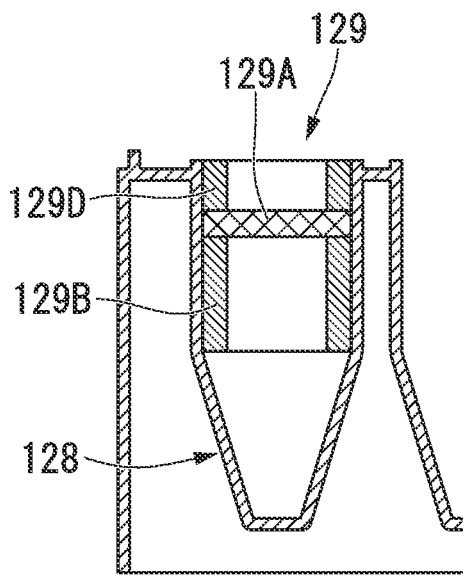
FIG. 6A is an enlarged cross-sectional view showing the structure of an oil-removing unit of the nucleic acid purification kit.
Figure 6B:
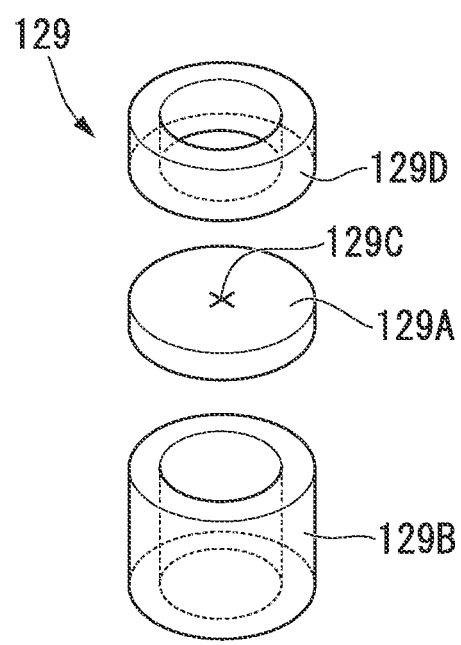
FIG. 6B is an exploded perspective view showing the structure of a part of the oil-removing unit.
Figure 7A:
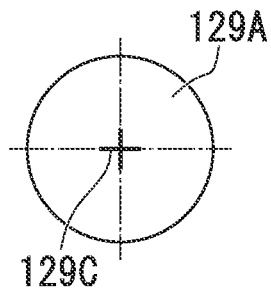
FIG. 7A is a plan view showing the structure of a part of the oil-removing unit.
Figure 7B:
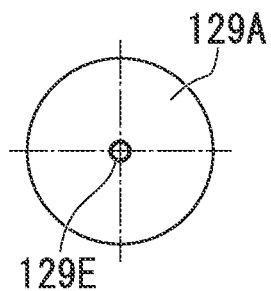
FIG. 7B is a plan view showing a modification of the structure of a part of the oil-removing unit.
Figure 7C:
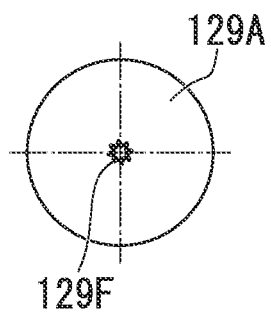
FIG. 7C is a plan view showing another modification of the structure of a part of the oil-removing unit.

The structure of the nucleic acid purification kit 10 will be described below with reference to FIGS. 3 to 7C. FIGS. 3 and 4 are perspective views showing the structure of the nucleic acid purification kit 10. Further, FIG. 5 is a cross-sectional view showing the structure of an extraction filter cartridge 150 of the nucleic acid purification kit 10. Furthermore, FIG. 6A is an enlarged cross-sectional view showing the structure of an oil-removing unit 128 of the nucleic acid purification kit 10, and FIG. 6B is an exploded perspective view showing the structure of a wiper 129. Moreover, FIGS. 7A, 7B, and FIG. 7C are plan views showing the structure of a part of the oil-removing unit 128.

As shown in FIG. 4, the nucleic acid purification kit 10 includes a reagent cartridge 100 in which a reagent or the like used to extract nucleic acid from a specimen is stored, and a dispensing chip rack (dispensing chip-receiver) 200 in which a plurality of dispensing chips (oil-dispensing chips and reagent-dispensing chips) 201 dispensing liquids are received. In this embodiment, the dispensing chip rack 200 includes the plurality of dispensing chips 201. Liquids, which are stored in the reagent cartridge 100, are dispensed or agitated by any one of the plurality of dispensing chips 201, so that cross-contamination does not occur between the liquids by the dispensing chips 201. Further, since the dispensing chip rack 200 is also a container in which the dispensing chips 201 having been used are collected, the dispensing chips 201 as infectious waste may be discarded from each dispensing chip rack 200 after the use of the dispensing chips 201 of the nucleic acid analyzer 1.

As shown in FIG. 3, the reagent cartridge 100 includes a body 101 that is formed in the shape of a box having an opening, and claw portions 102 that are formed so as to protrude laterally from the outer surface of the body 101. The claw portions 102 fix the reagent cartridge 100 to the specimen-introducing part 40 to be described below in the analyzer body 30.

It is preferable that a filmy sealing film 103 to be removed at the time of the use of the nucleic acid purification kit 10 be attached to a part of the outer surface of the body 101. The opening of the body 101 is sealed by the sealing film 103. Accordingly, it is possible to prevent the extraction filter cartridge 150 and the like, which are disposed in the body 101 and will be described below, from falling from the body 101. In addition, it is possible to prevent foreign materials such as dust from entering the body 101.

As shown in FIG. 4, a sample well (specimen storage portion) 110 in which a specimen such as a biological sample is put, a reagent well portion 120 in which reagents and the like used to extract nucleic acid from the specimen are stored, a waste liquid well (waste liquid storage portion) 130 to which unnecessary solution isolated in a process for extracting nucleic acid from the specimen is discarded, and a collection well 140 that collects the nucleic acid extracted from the specimen are integrally formed in the body 101.

Further, the reagent cartridge 100 includes the extraction filter cartridge 150 that contains a carrier adsorbing nucleic acid, and a holding portion 160 in which the extraction filter cartridge 150 is received is formed integrally with the reagent cartridge 100.

The reagent well portion 120 includes a plurality of reagent wells (reagent storage portions) 121, 122, 123, 124, 125, and 126; an oil well (oil storage portion) 127; and the oil-removing unit 128. Further, at the reagent well portion 120, openings of the plurality of reagent wells 121, 122, 123, 124, 125, and 126 and an opening of the oil well 127 are sealed by a sealing film 104 shown in FIG. 3. The penetration of gas to the body 101 is suppressed by the sealing film 104. Further, it is preferable that the sealing film 104 can be broken by being pierced by the dispensing chips 201. For example, a thin film made of metal, a plastic film, or the like may be used as the sealing film 104.

A solution 121A that dissolves biological materials such as the cell membrane, a solution 122A that dissolves biological materials such as the cytoplasm not completely dissolved in the solution 121A and causing the carrier to be clogged, washing solutions 123A and 124A that wash off undesired materials except for nucleic acid adsorbed on the carrier, an eluate 125A that elutes the nucleic acid from the carrier, and a diluted solution 126A that is used to adjust the concentration of the nucleic acid contained in the eluate are individually stored in the reagent wells 121 to 126, respectively.

Further, an analytical reagent will be provided in a nucleic acid analysis chip in the following use mode. However, there may be a method where an analytical reagent may be stored in a reagent well. For example, analytical reagent premixes where a part of a reagent used to measure SNP of nucleic acid by PCR (Polymerase Chain Reaction) and the invader (registered trademark) method is previously mixed may be individually stored in the respective reagent wells.

An analytical reagent premix is a mixed liquid that contains a base and a DNA polymerase for PCR, Cleavase (registered trademark) used in the invader (registered trademark) method, and a buffer used to perform PCR and a reaction using the invader (registered trademark) method together. It is preferable that the analytical reagent premix be stored in a reagent well so as to have a concentration higher than the optimum concentration at the time of a reaction in order to suppress enzyme activity while an analytical reagent premix is stored in a reagent well.

For example, a commonly known oil 127A, which is used while being superimposed on a reaction solution in a PCR reaction, is stored in the oil well 127. For example, mineral oil, silicon oil, and the like may be preferably employed as the oil 127A.

It is preferable that the oil-removing unit 128 include the wiper 129, which removes the oil 127A adhering to the outer surface of the dispensing chip 201 (see FIG. 4), therein as shown in FIG. 6A.

As shown in FIGS. 6A and 6B, the wiper 129 includes a wiping filter 129A that has a lipophilic property, and cylindrical support parts 129B and 129D that support the wiping filter 129A in the oil-removing unit 128. The wiping filter 129A is formed substantially in the shape of a column or a disc corresponding to the inner diameter of the oil-removing unit 128, and a slit 129C, which passes through the wiping filter in the direction of a central axis of the wiping filter 129A, is formed at the center of the wiping filter 129A.

As shown in FIG. 7A, the slit 129C is positioned at the center of the wiping filter 129A and formed in a cross shape when seen in the direction of the central axis. As shown in FIG. 7B, the wiping filter 129A may include a slit 129E, which is formed in a true circular shape when the wiping filter 129A is seen in the direction of the central axis, instead of the slit 129C. Further, as shown in FIG. 7C, the wiping filter 129A may include a circular slit 129F, which includes protruding portions protruding toward the inside in the radial direction of the wiping filter 129A, instead of the slit 129C.

As shown in FIG. 4, the waste liquid well 130 has a shape such that the extraction filter cartridge 150 can be supported at concave portions formed along the outer diameter shape of the extraction filter cartridge 150. While the extraction filter cartridge 150 is mounted in the waste liquid well 130, the extraction filter cartridge 150 does not fall down in the reagent cartridge 100.

Like the discard well 130, the collection well 140 has a shape such that the extraction filter cartridge 150 can be supported. The bottom portion of the collection well 140 has the shape of a container that can store a nucleic acid solution eluted from the carrier of the extraction filter cartridge 150 by the eluate 125A.

The waste liquid well 130 and the collection well 140 are disposed in the reagent cartridge 100 so as to be adjacent to each other. The reason for this disposition is to reduce the movement of the extraction filter cartridge 150 when the extraction filter cartridge 150 is moved to the collection well 140 after the extraction filter cartridge 150 is washed in the waste liquid well 130. Accordingly, it is possible to reduce the possibility of the extraction filter cartridge 150 passing above the reagent cartridge 100 contaminating the reagent cartridge 100 and the like.

As shown in FIG. 5, the extraction filter cartridge 150 includes a substantially cylindrical body 151 that forms an outer frame of the extraction filter cartridge, and an extraction filter unit 152 that is provided in the body 151.

All of upper and lower ends 151A and 151B of the body 151 are opened. Further, the body 151 is formed in the shape of a funnel so that the diameter of an opening of a portion of the body 151, which is closer to the lower end 151B than the extraction filter unit 152, is smaller than the diameter of the opening of the upper end 151A. A nozzle-like discharge port 151C is formed at the lower end 151B so as to protrude downward.

In this embodiment, the eluate 125A, the washing solutions 123A and 124A, the solution 121A where a specimen is dissolved, and the like are supplied from the opening of the upper end 151A, pass through the filter unit 152, and are discharged from the discharge port 151C.

The filter unit 152 includes an adsorption filter 152A that contains a carrier having a property to adsorb nucleic acid, and a support member 152B that is disposed closer to the lower end 151B than the adsorption filter 152A and prevents the adsorption filter 152A from being deformed.

The adsorption filter 152A is made of a porous material capable of adsorbing nucleic acid and formed in the shape of a film. It is preferable that a material having a property to adsorb nucleic acid in the washing solutions 123A and 124A and adsorb less nucleic acid in the eluate 125A be used as the material of the adsorption filter 152A. Further, it is preferable that the adsorption filter 152A be made of a porous material to which a hydroxyl group is introduced as a hydrophilic group. Specifically, the adsorption filter 152A is made of silica or a material coated with silica. As long as a material capable of adsorbing a biological material in the presence of an organic material is used as the material of the adsorption filter 152A, the material of the adsorption filter 152A is not particularly limited. Furthermore, the adsorption filter 152A is formed by superimposing fibrous materials such as glass wool, so that the adsorption filter 152A may have porosity.

It is preferable that the support member 152B be made of a material having low adsorbability for at least nucleic acid and not inhibiting a reaction for extracting nucleic acid from a specimen. For example, the support member 152B may be formed so as to have porosity by the sintering of resin particles. The rigidity of the support member 152B is higher than that of the adsorption filter 152A, so that the deformation of the adsorption filter 152A in the body 151 is suppressed by the support member 152B.

It is preferable that an absorbent body (not shown), which absorbs liquid, be provided at the bottom portion of the holding portion 160 shown in FIG. 4. In this case, when the extraction filter cartridge 150 is received in the holding portion 160, the absorbent body comes into contact with the outer surface of the extraction filter cartridge 150 corresponding to the discharge port 151C. Accordingly, for example, when the washing solution 123A adheres to the outer surface of the discharge port 151C while the washing solution 123A is supplied to the extraction filter cartridge 150, it is possible to remove the washing solution 123A by making the washing solution 123A be absorbed in the absorbent body.

Figure 8B:
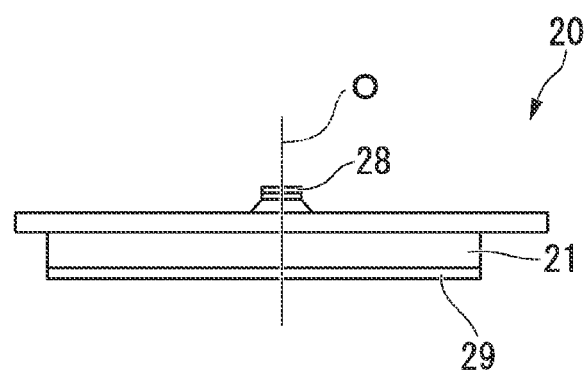
FIG. 8B is a side view of the structure of the nucleic acid analysis chip.
Figure 8C:
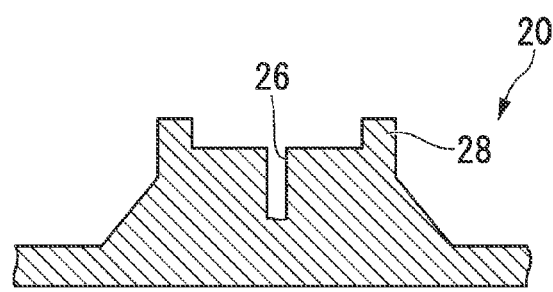
FIG. 8C is an enlarged cross-sectional view showing an injection port of the structure of the nucleic acid analysis chip.

The structure of the nucleic acid analysis chip 20 will be described below with reference to FIGS. 8A to 8C. The nucleic acid analysis chip 20 includes a disc-like chip body 21 and a lid body 29 that is attached to the chip body 21.

The chip body 21 includes the plurality of reaction containers 22 that are arranged in the circumferential direction of the chip body 21 so as to be at the same distance from the center of the chip body 21, and passages 23 that are formed on the chip body 21 so as to communicate with each of the reaction containers 22. In this embodiment, twenty-three reaction containers 22 are formed at the chip body 21.

Further, an injection port 26 through which a nucleic acid solution or the like containing the nucleic acid purified by the above-mentioned nucleic acid purification kit 10 is fed to the reaction container 22, and an outlet 27 that is formed near the injection port 26 are formed at the central portion of the chip body 21. The injection port 26 and the outlet 27 communicate with the flow passages 23. Furthermore, a protruding wall portion 28, which protrudes from the outer surface of the chip body 21 so as to surround the injection port 26 and the outlet 27, is formed on the chip body 21.

It is preferable that the material of the chip body 21 be a material not affecting the analysis of nucleic acid. Specifically, it is preferable that the material of the chip body 21 be a resin material containing at least one or more of polypropylene, polycarbonate, and acryl. Homopolypropylene or a random copolymer of polypropylene and polyethylene may be used as polypropylene. Further, a copolymer of polymethyl methacrylate or methyl methacrylate and a monomer such as other methacrylic ester, acrylic ester, or styrene may be used as acryl.

It is preferable that the chip body 21 have optical transparency at the portions of at least the reaction container 22, and it is preferable that fluorescence, coloring, or the like generated by a biochemical reaction occurring in the reaction containers 22 be detectable from the outside of the reaction containers 22. Specifically, it is preferable that the chip body transmit light in a visible light region (wavelength is in the range of 350 nm to 780 nm) at a light transmittance of 70% or more. Moreover, the chip body 21 may be made of a resin material having optical transparency.

The reaction containers 22 are formed at the chip body 21 as substantially hemispherical-concave portions that can store liquid therein. Reagents, which are used to perform biochemical reactions, are provided on the inner wall surfaces of the reaction containers 22. Specifically, at least a pair of primer sets that amplifies a gene region containing SNP, which is an object to be tested, and invader (registered trademark) oligos and signal probes that are used in the invader (registered trademark) method are received in each of the reaction containers 22. It is preferable that plural kinds of primer sets, invader (registered trademark) oligos, and signal probes, which vary according to a gene region, that is, an object to be tested, be previously disposed in each of the reaction containers 22. In this case, it is possible to measure different kinds of SNPs for every reaction container 22. Further, according to, for example, the nucleic acid analysis chips 20 of this embodiment, it is possible to simultaneously measure twenty-three kinds of SNPs.

Concave portions are formed on the chip body 21 on the inner side of the reaction containers 22 in the radial direction, so that the passages 23 are formed. Further, each of the flow passages 23 includes a main flow passage 24 and a branch flow passage 25. The main flow passage 24 is formed so as to extend in the circumferential direction of the chip body 21 while meandering between the center of the chip body 21 and the outer portion of the chip body 21 in the radial direction. The branch flow passage 25 is branched from the main flow passage 24 so as to communicate with the main flow passage 24 and the reaction container 22.

One end 24A of the main flow passage 24 communicates with the injection port 26, and the other end 24B of the main flow passage 24 communicates with the outlet 27. Further, the main flow passage 24 is formed between the reaction containers 22, which are adjacent to each other in the circumferential direction of the chip body 21, so as to have a chevron shape 24C that protrudes along the central axis O. Since the main flow passage 24 is formed between the reaction containers 22 that are adjacent to each other in the circumferential direction of the chip body 21 and has a chevron shape 24C in the direction of the central axis O, liquid stored in the main flow passages 24 is interrupted at the apexes 24D of the chevron shapes 24C and fed to each of the reaction containers 22 when the nucleic acid analysis chip 20 is rotated about the central axis O.

The branch flow passage 25 is formed so that the area of a portion of the branch flow passage connected to the main flow passage 24 is smaller than the area of the main flow passage 24. A portion of the branch flow passage 25 connected to the main flow passage 24 forms a flow restricting portion 25A that restricts the liquid flowing to the branch flow passage 25 from the main flow passage 24.

The lid body 29 is provided on the side of the chip body 21 where the reaction containers 22 and the flow passages 23 are formed. The lid body 29 is attached to the chip body 21, so that concave portions forming the reaction containers 22 and the flow passages 23 are lidded. Accordingly, independent reaction spaces and flow passages are formed.

It is preferable that the material of the lid body 29 be a material having high thermal conductivity. Metal materials, such as aluminum, copper, silver, nickel, brass, and gold, may be employed as the material of the lid body 29. A portion having thermal conductivity may be at a portion of the lid body where at least reaction containers 22 are positioned. Further, as long as heat can be transferred to a liquid or the like in the reaction containers 22 at a sufficient ratio during the biochemical reactions (for example, PCR reactions) in the reaction containers 22, the lid body 29 may be formed of a thin plate made of the same resin material as the resin material of the above-mentioned chip body 21.

The nucleic acid analysis chip 20 of this embodiment feeds liquid, which is stored in the main flow passages 24, to the respective branch flow passages 25 and feeds the liquid to each of the reaction containers 22 through the branch flow passages 25 through centrifugal force that is generated due to the rotation of the nucleic acid analysis chip 20 about the central axis O.

The structure of the analyzer body 30 will be described below with reference to FIG. 2.

The analyzer body 30 includes the specimen-introducing part 40 where the above-mentioned nucleic acid purification kit 10 and the above-mentioned nucleic acid analysis chip 20 are disposed, the purification treatment unit 50 that performs an operation for extracting nucleic acid from a specimen by the nucleic acid purification kit 10, the centrifugal liquid feed unit 60 that rotates the nucleic acid analysis chip 20 about the central axis O, and the analysis unit 70 that analyzes nucleic acid in the reaction containers 22 of the nucleic acid analysis chip 20.

The specimen-introducing part 40 includes a tray 41 where the reagent cartridge 100 and the dispensing chip rack 200 of the nucleic acid purification kit 10 are disposed, and the analysis chip holder 42 where the nucleic acid analysis chip 20 is placed.

Since the tray 41 is detachably mounted on the specimen-introducing part 40, the tray can be sterilized or discarded as infectious waste when a specimen or the like adheres to the tray. Further, since the tray 41 is provided with engagement portions 43 with which the above-mentioned claw portions 102 formed at the reagent cartridge 100 are engaged, the reagent cartridge 100 does not fall down on the tray 41. In this embodiment, the claw portions 102 serve as a positioning mechanism that positions the reagent cartridge 100 on the specimen-introducing part 40.

The nucleic acid analysis chip 20 is fitted to a circular through-hole, so that the analysis chip holder 42 can support the nucleic acid analysis chip 20.

The purification treatment unit 50 includes a dispensing section 52 that transports the dispensing chips 201 disposed in the dispensing chip rack 200 and sucks, holds, and discharges liquid by using a robot hand 51 and the dispensing chips 201; and a pressurizing section 53 that pressurizes the inner portion of the extraction filter cartridge 150 by making air flow into the extraction filter cartridge from the upper end of the extraction filter cartridge 150 received in the reagent cartridge 100.

Figure 10:
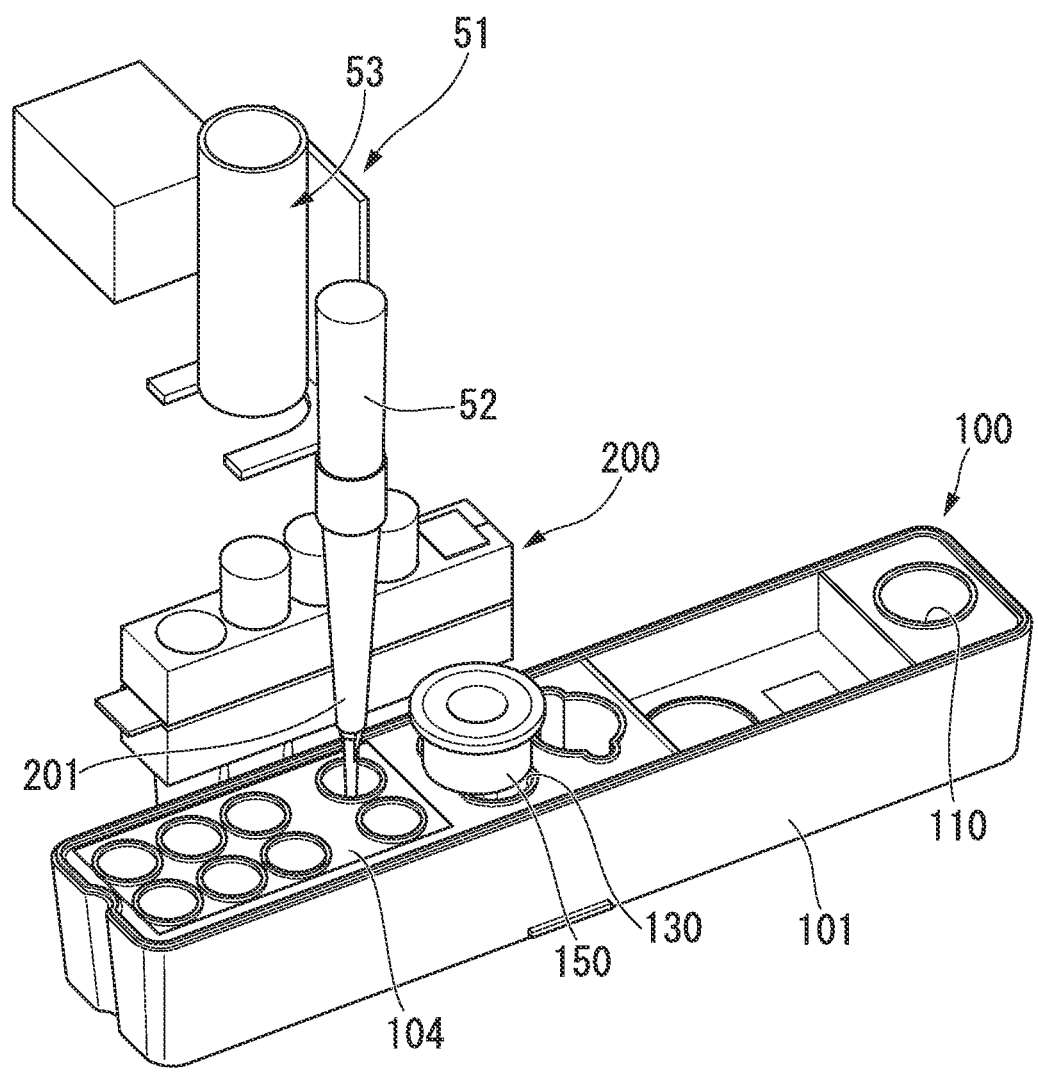
FIG. 10 is a view illustrating the operation of the nucleic acid analyzer that purifies nucleic acid.
Figure 11:
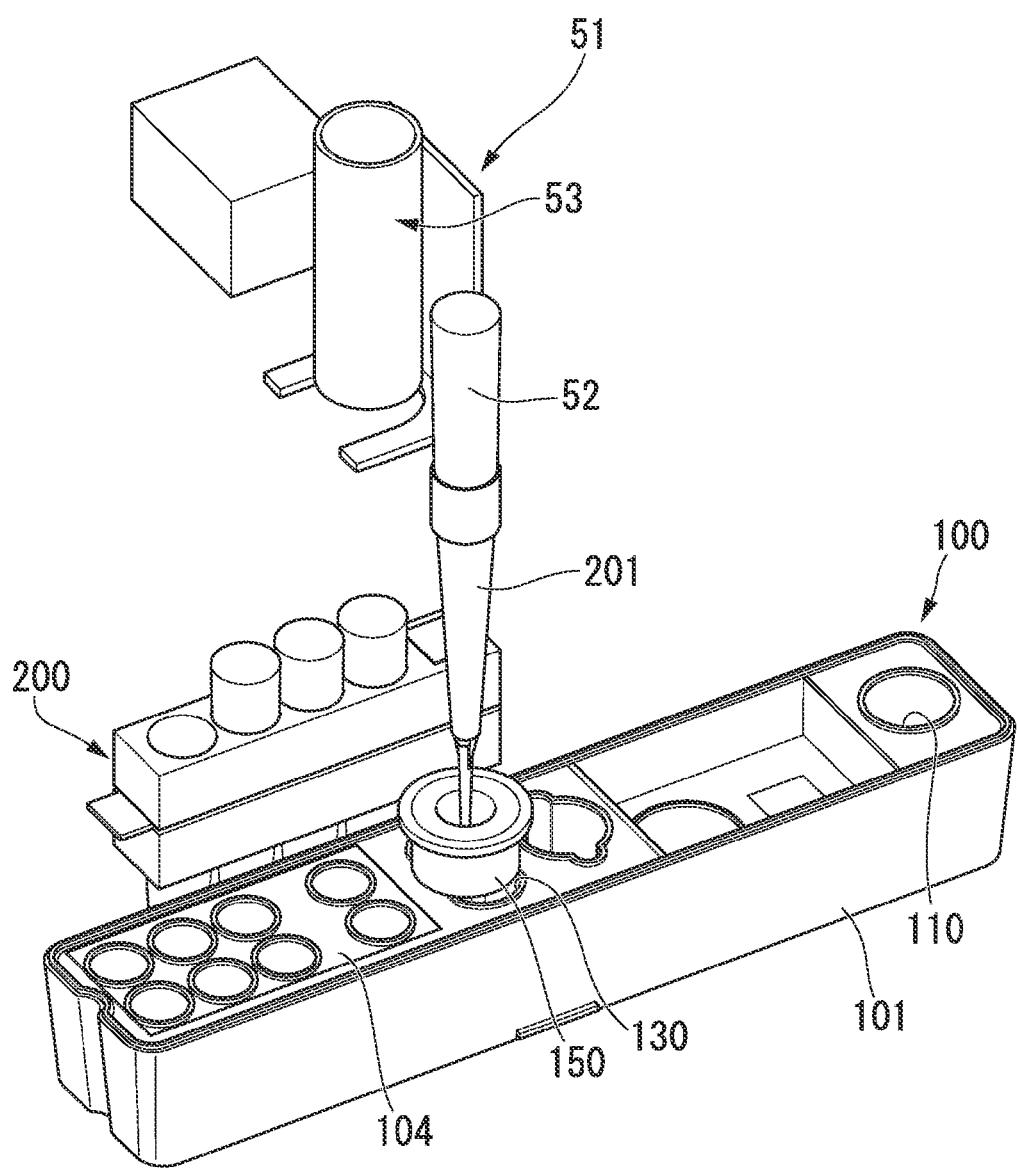
FIG. 11 is a view illustrating the operation of the nucleic acid analyzer that purifies nucleic acid.

The dispensing chip 201 is detachably connected to the dispensing section 52 by press-fitting. In this state, liquid is dispensed or transferred by the dispensing chip 201 (FIGS. 10 and 11). Further, the plurality of dispensing chips 201 are prepared, and are appropriately replaced to prevent contamination.

When the dispensing chip 201 is to be replaced, it is possible to open the dispensing chip 201 from the dispensing section 52 by pushing down the upper end of the dispensing chip 201 with a release portion (not shown). The dispensing section 52 is provided with the release portion. For example, a protruding portion, which is easily engaged with the release portion, may be formed at the upper end of the dispensing chip 201.

Figure 12:
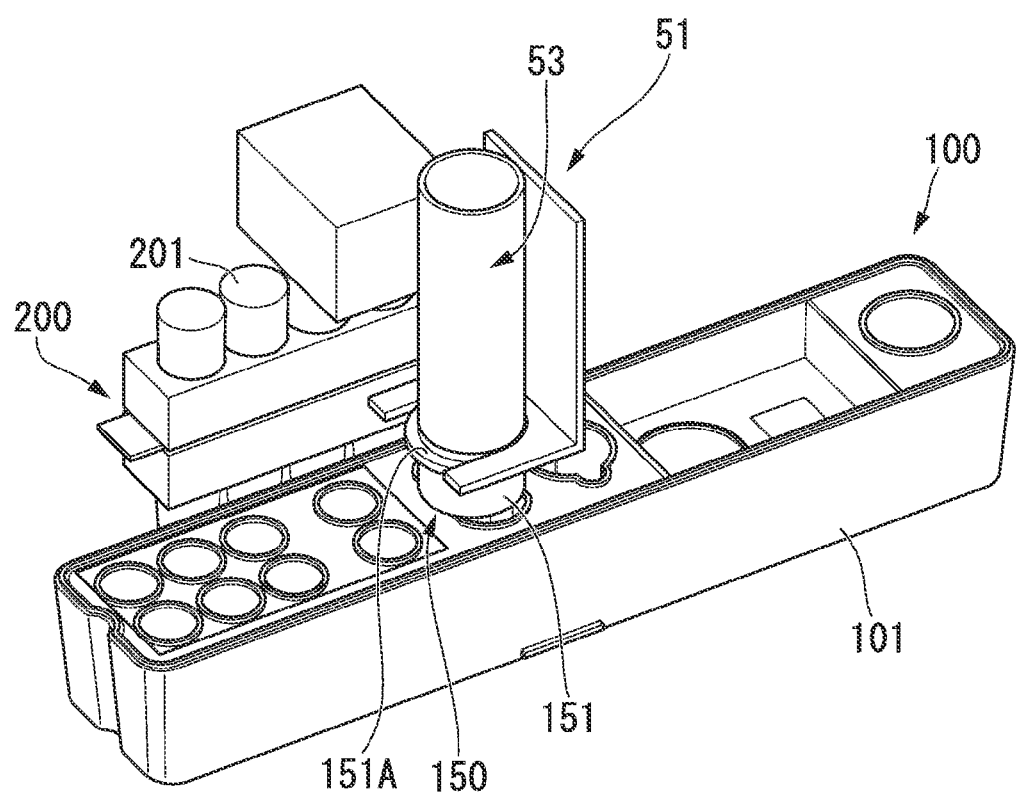
FIG. 12 is a view illustrating the operation of the nucleic acid analyzer that purifies nucleic acid.

The extraction filter cartridge 150 is moved by the robot hand 51 and is pressurized by the pressurizing section 53. During this pressurization, the pressurizing section 53 and the extraction filter cartridge 150 can be air-tightly engaged with each other (FIG. 12). Examples of the structure, which is suitable for making the pressurizing section and the extraction filter cartridge be air-tightly engaged with each other, include a structure where an elastic member is provided at the lower end of the pressurizing section 53 or the upper end 151A of the extraction filter cartridge 150. It is possible to pressurize the inner portion of the extraction filter cartridge 150 by the pressurizing section 53 while the pressurizing section 53 and the extraction filter cartridge 150 are engaged as described above.

A well-known centrifugal device may be appropriately employed as the centrifugal liquid feed unit 60, and the centrifugal liquid feed unit 60 can support the nucleic acid analysis chip 20 and rotate the nucleic acid analysis chip 20 about the central axis O. It is preferable that the rotational speed of the nucleic acid analysis chip 20 rotated by the centrifugal liquid feed unit 60 be substantially equal to a speed where liquid flows into the branch flow passages 25 from the main flow passages 24 through centrifugal force applied to the liquid supplied into the nucleic acid analysis chip 20. The optimum rotational speed of the nucleic acid analysis chip depends on the shape of the nucleic acid analysis chip. For example, in the case of the nucleic acid analysis chip 20 of this embodiment, it is preferable that the rotational speed of the nucleic acid analysis chip 20 rotated by the centrifugal liquid feed unit 60 be 1000 rpm or more.

The analysis unit 70 includes a temperature control mechanism 80 that comes into contact with the nucleic acid analysis chip 20 and changes the temperature in the reaction container 22 of the nucleic acid analysis chip 20 so that the temperature in the reaction container 22 corresponds to a predetermined temperature change; and a fluorescence measuring section 90 that measures fluorescence in the reaction container 22 of the nucleic acid analysis chip 20.

Figure 16:
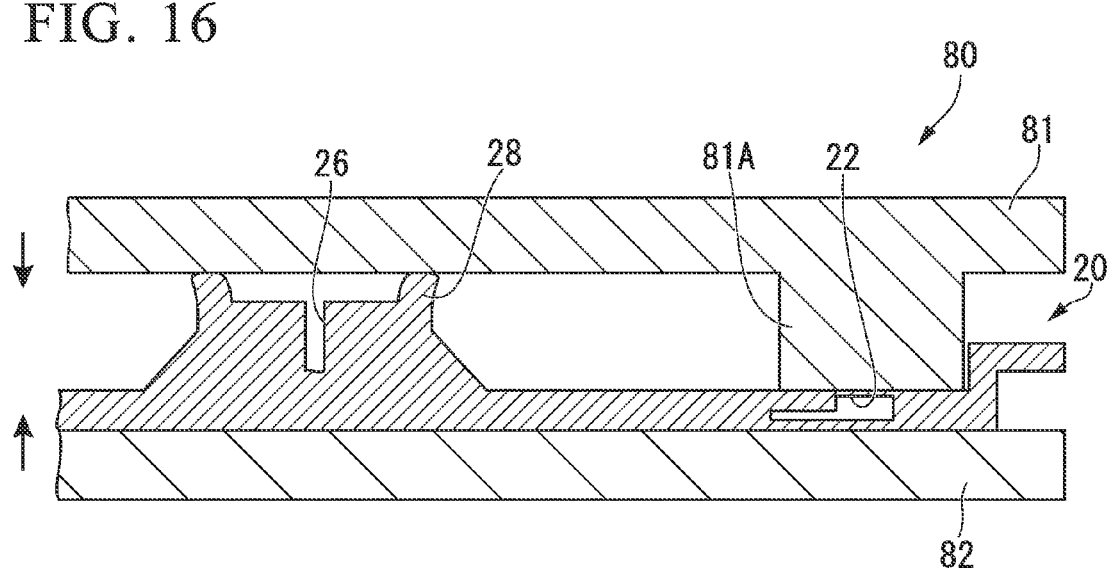
FIG. 16 is a cross-sectional view illustrating the action of the nucleic acid analysis chip of the nucleic acid analyzer.

The temperature control mechanism 80 includes upper and lower heat plates 81 and 82 that have flat surfaces facing each other, and a temperature adjustment controller (not shown). Although the details of the temperature control mechanism will be described below, the nucleic acid analysis chip 20 is interposed between the upper and lower heat plates 81 and 82 as shown in FIG. 16. A ring-shaped convex region 81A is formed on the upper heat plate 81. Due to this convex region 81A, the upper heat plate 81 comes into contact with at least the region of the nucleic acid analysis chip 20 corresponding to the reaction solution 22 and the protruding wall portion 28. Metal materials having a high thermal conductivity, such as aluminum, gold, silver, and copper, may be used for the upper and lower heat plates 81 and 82. Further, to increase adhesion between the nucleic acid analysis chip 20 and the heat plates, the surface of each of the heat plates, which comes into contact with the nucleic acid analysis chip, may be formed of an elastic body having excellent thermal conductivity.

The temperatures of the upper and lower heat plates 81 and 82 are changed according to the temperature change that is previously set in the above-mentioned temperature adjustment controller. A temperature control method of a commonly known thermal cycler may be appropriately employed as a temperature control method of the temperature adjustment controller. Accordingly, it is possible to perform PCR and a reaction, which uses the invader (registered trademark) method, in the reaction container 22 of the nucleic acid analysis chip 20.

The fluorescence measuring section 90 measures the fluorescence intensity of a fluorescent material by emitting excitation light, which excites the fluorescent material contained in the reaction container 22, to the reaction container 22 through an optical fiber (not shown) from an optical part 91 that includes a light source part such as LED or a light receiving part such as PMT, and an optical filter for excitation or a light receiving optical filter. It is possible to obtain an arbitrary wavelength of excitation light through the combination of light sources or filters.

Further, the analyzer body 30 includes a transport unit (transport part) 55 that moves the specimen-introducing part 40 and the analysis unit 70 in the housing 31. A transport unit, which includes rails 56 provided in the housing 31 and a moving stage 57 moving along the rails 56, may be employed as an example of the transport unit 55. Further, the specimen-introducing part 40 and the analysis unit 70 may be moved in the housing 31 by the robot hand 51 other than the transport unit 55. Furthermore, the transport part of the invention is not limited to the example; and the specimen-introducing part 40 where the nucleic acid purification kit 10 and the nucleic acid analysis chip 20 are disposed may include a mechanism that is transported so as to be capable of being treated by the purification treatment unit 50, the centrifugal liquid feed unit 60, and the analysis unit 70, respectively. For example, the purification treatment unit 50, the centrifugal liquid feed unit 60, and the analysis unit 70 may move so that the specimen-introducing part 40 is relatively transported to each of the treatment units.

In the example of the nucleic acid analyzer 1 according to this embodiment having the structure shown in FIG. 2, the specimen-introducing part 40 can be linearly moved in the housing 31 of the analyzer body 30 in the X direction shown in FIG. 2 by the transport unit and can be moved up to the positions of the purification treatment unit 50, the centrifugal liquid feed unit 60, and the analysis unit 70. Moreover, the analysis unit 70 includes a moving mechanism of the analysis unit 70 as transport part that is separate from the transport unit of the specimen-introducing part 40. The analysis unit can be linearly moved in the housing 31 of the analyzer body 30 in the Y direction shown in FIG. 2 by this moving mechanism. Accordingly, it is possible to switch the treatment units, which perform treatments on the nucleic acid analysis chip 20, to the temperature control mechanism 80 and the fluorescence measuring section 90. Specifically, the temperature of the nucleic acid analysis chip 20 is controlled by the upper and lower heat plates 81 and 82 at the time of a PCR reaction and the upper heat plate 81 is moved in the Y direction before the invader reaction, so that an optical fiber is positioned above the nucleic acid analysis chip 20. Therefore, while the temperature of the nucleic acid analysis chip is controlled to the invader reaction temperature by the lower heat plate 82, the optical fiber is moved above the nucleic acid analysis chip 20 and the fluorescence intensity in the reaction container 22 can be measured.

Figure 17:
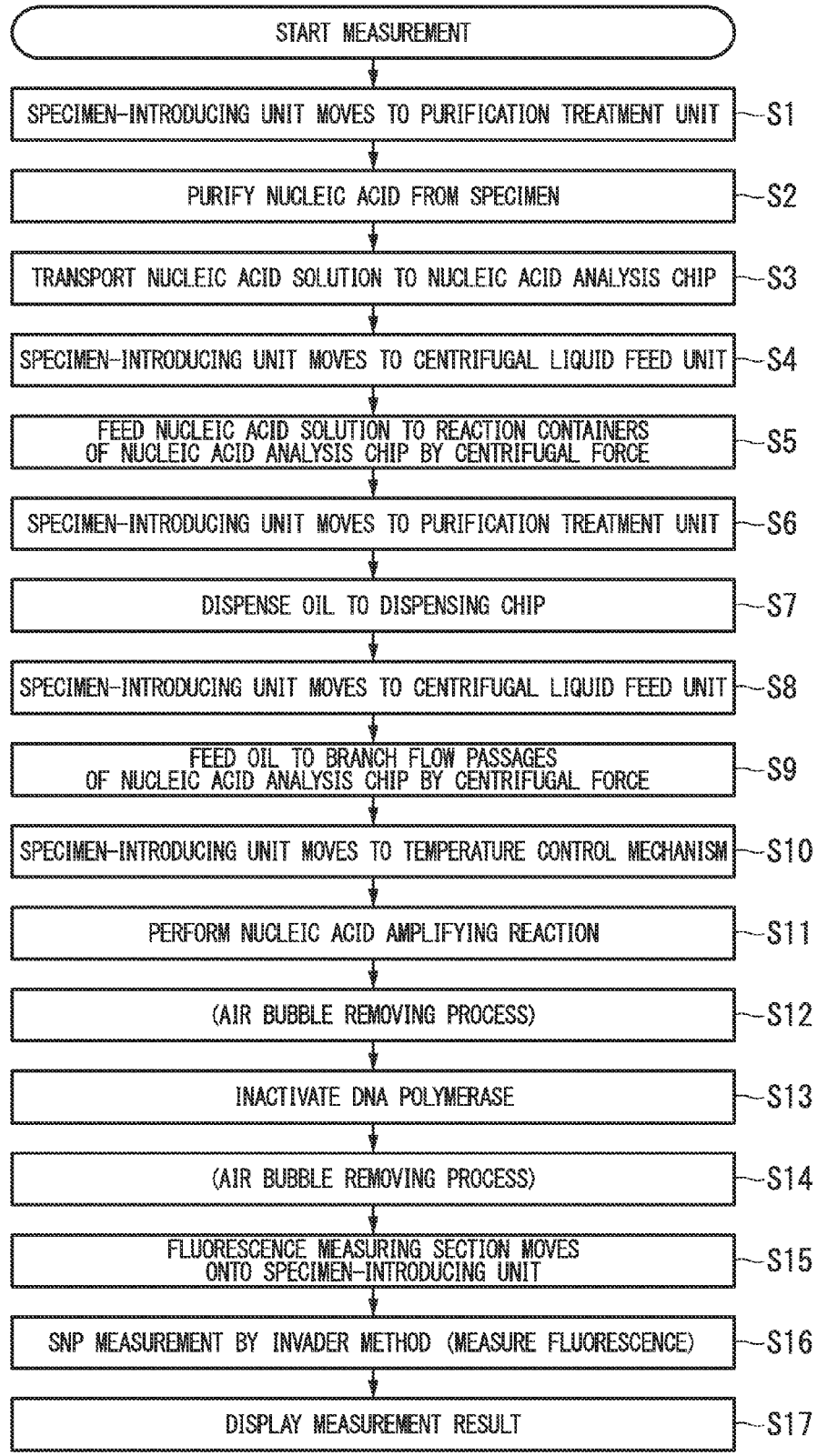
FIG. 17 is a flowchart illustrating the operation of the nucleic acid analyzer at the time of the use of the nucleic acid analyzer.

The operation of the nucleic acid analyzer 1 according to this embodiment having the above-mentioned structure at the time of the use of the nucleic acid analyzer will be described with reference to a flowchart of FIG. 17.

First, the sealing film 103 of the reagent cartridge 100 shown in FIG. 3 is manually removed by a user before the nucleic acid analyzer 1 is operated. Subsequently, for example, a whole blood sample is manually injected to the sample well 110 of the reagent cartridge 100 by the user. Then, the user places the reagent cartridge 100 and the dispensing chip rack 200 on the tray 41 as shown in FIG. 2. At this time, the claw portions 102 formed at the reagent cartridge 100 are engaged with the engagement portions 43 of the tray 41, so that the reagent cartridge 100 is fixed to the tray 41.

In addition, the nucleic acid analysis chip 20 is manually placed on the analysis chip holder 42 by the user.

Figure 9:
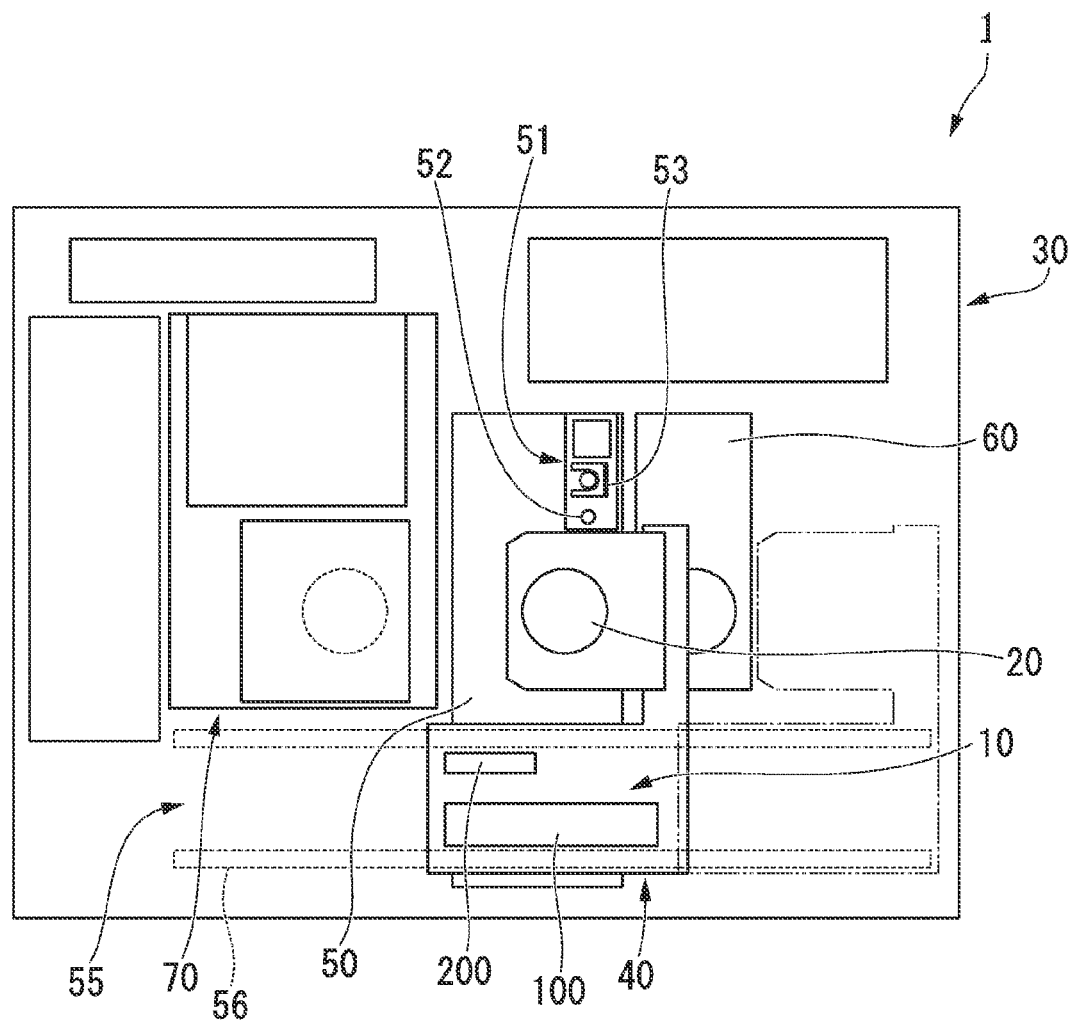
FIG. 9 is a view illustrating the operation of the nucleic acid analyzer at the time of the use of the nucleic acid analyzer.

Subsequently, as shown in FIG. 9, the specimen-introducing part 40 is moved to the purification treatment unit 50 (S1). As shown in FIG. 10, the dispensing section 52 is moved in the purification treatment unit 50. Various reagents, which are stored in the reagent wells 121 to 126, are put into or taken from the dispensing chips 201 according to a predetermined procedure by the dispensing section 52 through the supply of air (pressurization) or the suction of air (depressurization); are dispensed; and are mixed. Accordingly, cells in the whole blood sample, which is supplied to the sample well 110, are dissolved, so that a cell solution is obtained. For the suction of liquid into the dispensing chips 201 from the reagent wells 121 to 126, the ends of the dispensing chips 201 are inserted into the sealing film 104 that seals the reagent wells 121 to 126. Through-holes are formed at the sealing film 104, and various reagents stored in the reagent wells 121 to 126 are sucked by the dispensing chips 201.

Subsequently, the extraction filter cartridge 150 is transported to the waste liquid well 130, and a solution in which the cells are dissolved is supplied to the extraction filter cartridge 150 as shown in FIG. 11. After that, as shown in FIG. 12, the dispensing chip 201 returns to the dispensing chip rack 200 and the pressurizing section 53 then comes into contact with the upper end 151A of the extraction filter cartridge 150. Further, the pressurizing section 53 supplies gas into the extraction filter cartridge 150 from the upper end 151A of the extraction filter cartridge 150 so that liquid passes through the adsorption filter 152A. It is possible to increase the speed of liquid, which passes through the adsorption filter 152A, by pressurizing the extraction filter cartridge body 151 by the pressurizing section 53 as described above. The solution in which the cells are dissolved passes through the adsorption filter 152A and nucleic acid is adsorbed on the adsorption filter 152A. After that, the adsorption filter 152A is washed with the solution 122A that dissolves biological materials. The biological materials are cytoplasm and the like that are not completely dissolved in the solution 121A and cause the carrier to be clogged.

In addition, the washing solutions 123A and 124A are supplied to the adsorption filter 152A and the adsorption filter 152A is washed with the washing solutions 123A and 124A. After that, the extraction filter cartridge 150 is transported to the collection well 140 by the robot hand 51, and the eluate 125A is supplied to the adsorption filter 152A by the dispensing section 52 and the dispensing chips 201. Accordingly, nucleic acid, which has been adsorbed on the adsorption filter 152A, is eluted in the eluate 125A, and a nucleic acid solution containing nucleic acid is collected at the collection well 140. In this case, it is preferable that the time taken to collect the nucleic acid solution be shortened by pressurizing the adsorption filter 152A by the robot hand 51 and the pressurizing section 53.

Moreover, the diluted solution 126A is blended with the eluate 125A containing nucleic acid, so that the preparation of a sample is completed.

The isolation and purification of nucleic acid, which are performed by the nucleic acid purification kit 10, are completed in this way.

When nucleic acid is purified from a specimen by the nucleic acid purification kit 10 (S2), the nucleic acid solution containing nucleic acid is transported to the nucleic acid analysis chip 20 from the collection well 140 with the dispensing chip 201 by the dispensing section 52 (S3). In addition, the nucleic acid solution is fed to the main flow passages 24 of the nucleic acid analysis chip 20 from the injection port 26 of the nucleic acid analysis chip 20. At this time, the nucleic acid solution does not flow into the branch flow passages 25 from the main flow passages 24.

Figure 13:
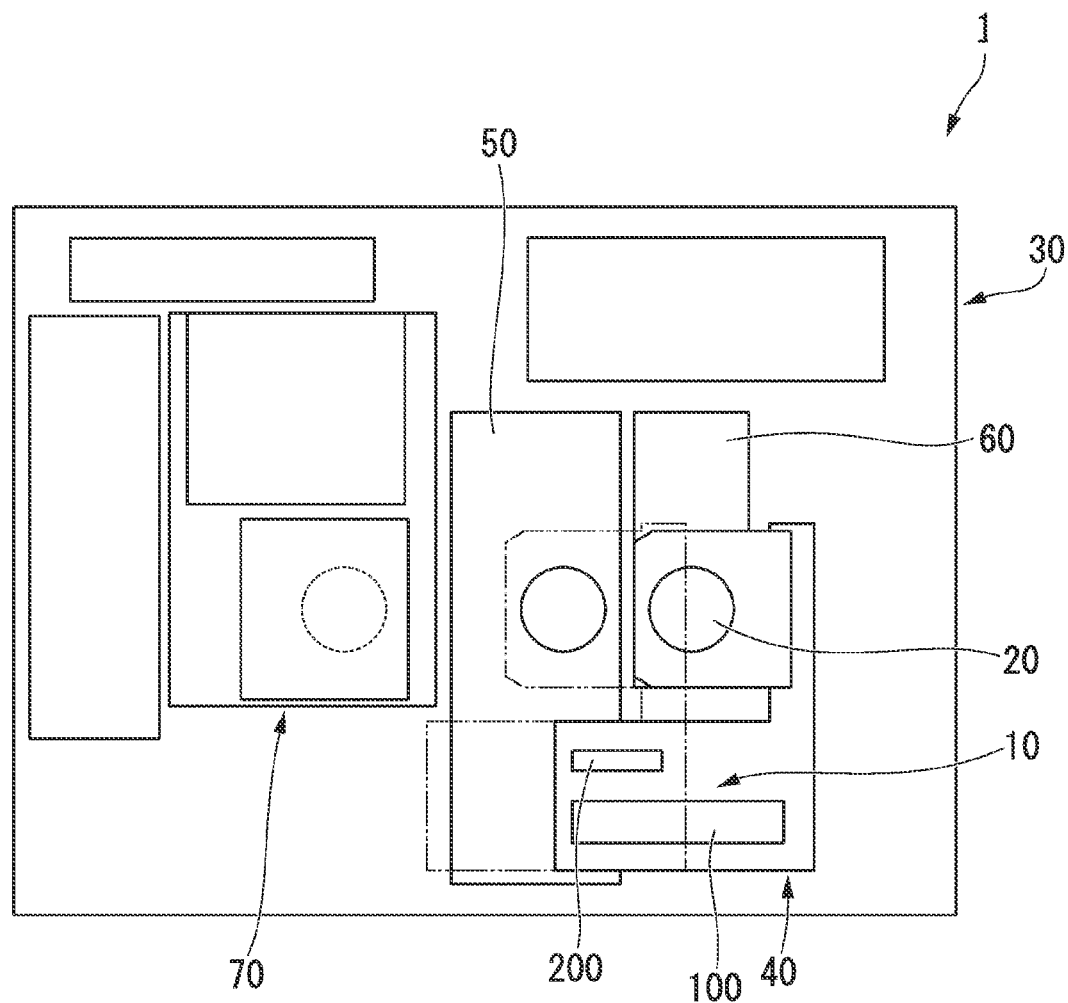
FIG. 13 is a view illustrating the operation of the nucleic acid analyzer at the time of the use of the nucleic acid analyzer.

While the nucleic acid analysis chip 20 is placed on the specimen-introducing part, the specimen-introducing part 40 is moved to the centrifugal liquid feed unit 60 as shown in FIG. 13 (S4). In addition, when the nucleic acid analysis chip 20 is rotated about the central axis O by the centrifugal liquid feed unit 60 and a centrifugal force is applied to the nucleic acid solution stored in the main flow passages 24 of the nucleic acid analysis chip 20, the nucleic acid solution is fed to each of the reaction containers 22 of the nucleic acid analysis chip 20 (S5).

When the nucleic acid solution is completely fed by the centrifugal liquid feed unit 60, the specimen-introducing part 40 is moved to the purification treatment unit 50 again while the nucleic acid analysis chip 20 is placed on the specimen-introducing part (see FIG. 9, S6). At the purification treatment unit 50, the oil 127A, which is stored in the oil well 127 of the nucleic acid extraction kit 10 shown in FIG. 4, is sucked into the dispensing chip 201. At this time, since the material of the dispensing chip 201 has high affinity with the oil 127A, the oil 127A may adhere to the outer surface of the dispensing chip 201 in the shape of a drop as shown in FIG. 14A.

Figure 14A:
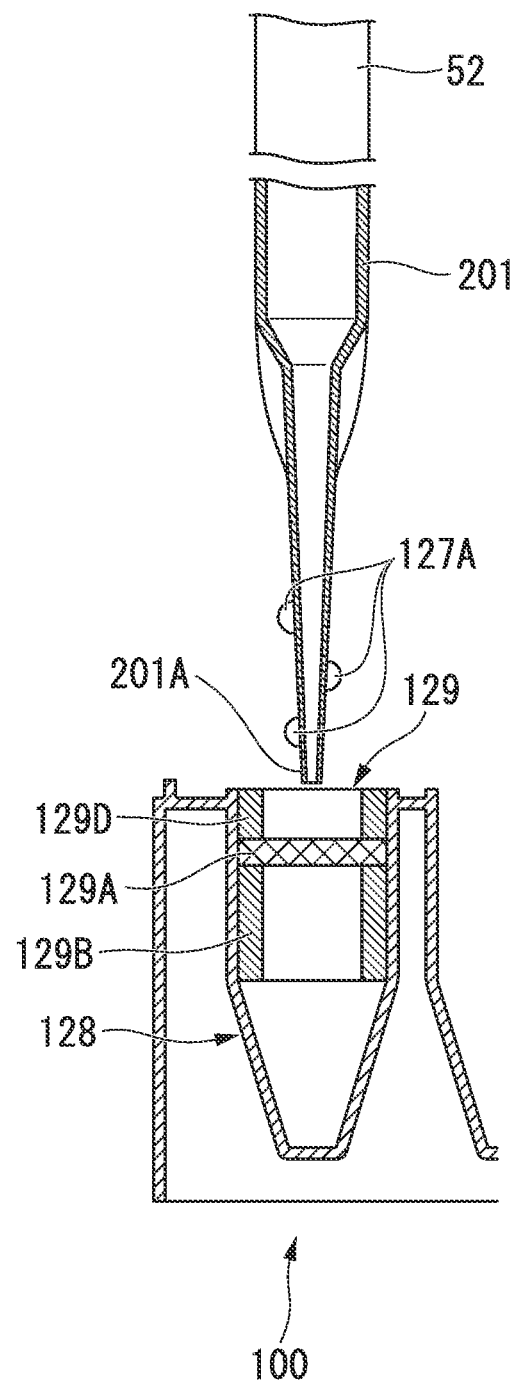
FIG. 14A is a cross-sectional view illustrating the action of the oil-removing unit of the nucleic acid analyzer.
Figure 14B:
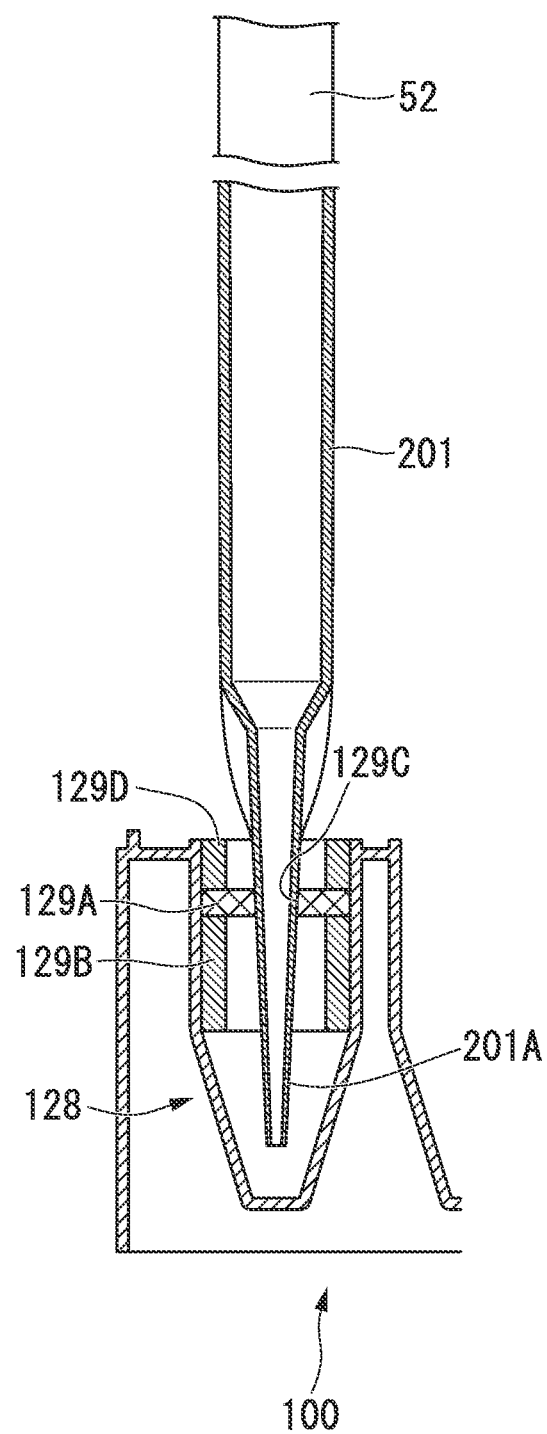
FIG. 14B is a cross-sectional view illustrating the action of the oil-removing unit of the nucleic acid analyzer.
Figure 15:
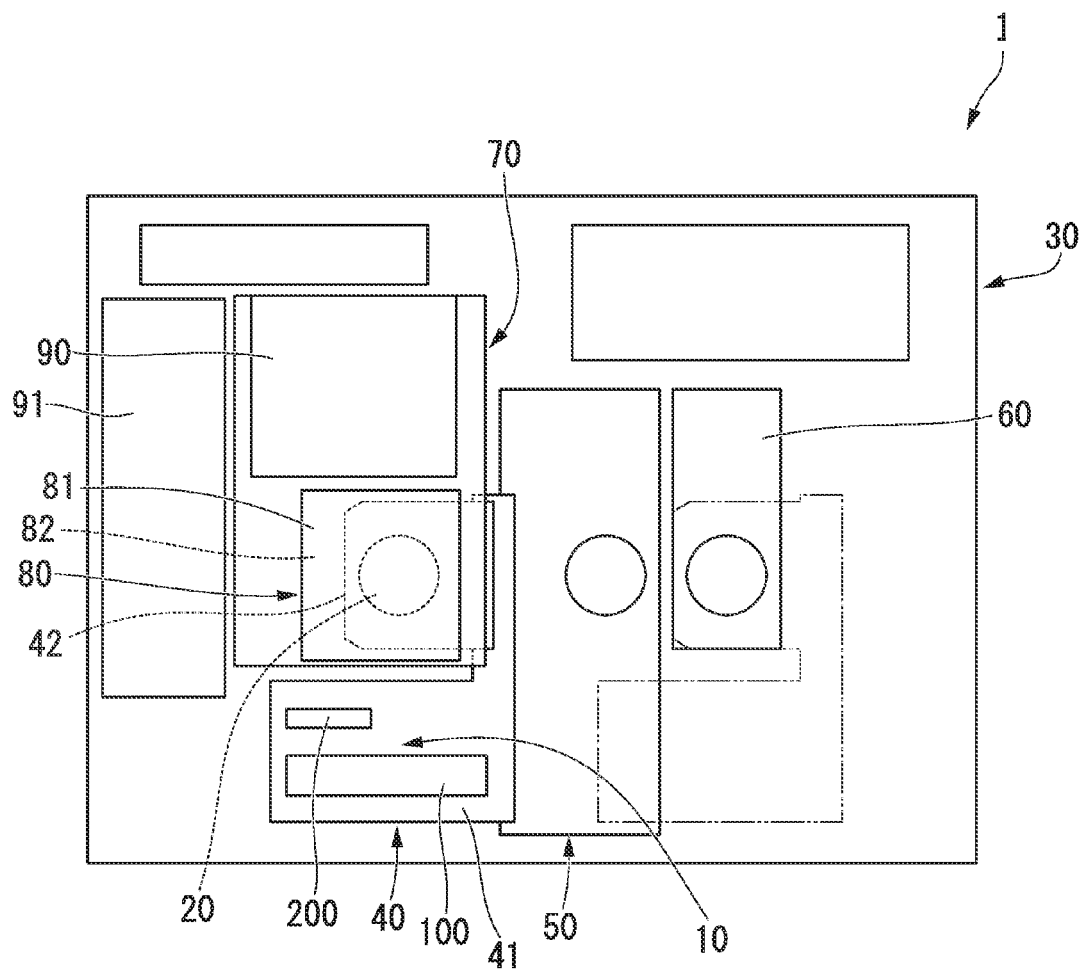
FIG. 15 is a view illustrating the operation of the nucleic acid analyzer at the time of the use of the nucleic acid analyzer.

The dispensing section 52 moves the dispensing chip 201 to the oil-removing unit 128 as shown in FIG. 14A. In addition, as shown in FIG. 14B, the dispensing section 52 inserts an end 201A of the dispensing chip 201 into the slit 129C of the wiping filter 129A of the oil-removing unit 128. The oil 127A, which adheres to the outer peripheral surface of the end 201A of the dispensing chip 201, is absorbed in the wiping filter 129A and removed from the outer peripheral surface of the dispensing chip 201. When the dispensing chip 201 is taken out of the slit 129C, the outer peripheral surface of the dispensing chip 201 comes into contact with the wiping filter 129A again. Accordingly, the oil 127A adhering to the outer peripheral surface of the dispensing chip 201 is wiped off.

The dispensing chip 201, which holds the oil 127A therein and where the oil 127A of the outer peripheral surface has been removed, is transported to the nucleic acid analysis chip 20 by the dispensing section 52. Moreover, the end 201A of the dispensing chip 201 is inserted into the injection port 26 of the nucleic acid analysis chip 20 shown in FIG. 8A and the oil 127A is fed to the main flow passages 24 from the injection port 26 (S7). At this time, the main flow passages 24 are filled with the oil 127A, but the oil 127A does not flow into the branch flow passages 25.

When the oil 127A is supplied to the main flow passages 24, the specimen-introducing part 40 is moved to the centrifugal liquid feed unit 60 again while the nucleic acid analysis chip 20 is placed on the specimen-introducing part (see FIG. 13, S8). Moreover, the nucleic acid analysis chip 20 is rotated about the central axis O by the centrifugal liquid feed unit 60. When a centrifugal force is applied to the oil 127A stored in the main flow passages 24 of the nucleic acid analysis chip 20 shown in FIG. 8A, the oil 127A is substituted with air of the branch flow passages 25 and the respective branch flow passages 25 are filled with the oil 127A (S9). The specific gravity of the oil 127A is smaller than that of the nucleic acid solution. While equivalent acceleration is applied to the oil 127A and the nucleic acid solution by the centrifugal liquid feed unit 60, the nucleic acid solution is positioned at the outer portion of the nucleic acid analysis chip 20 in the radial direction. Accordingly, while the reaction containers 22 are filled with the nucleic acid solution, the oil 127A does not flow into the reaction containers 22.

When the oil 127A is fed to the branch flow passages 25, the specimen-introducing part 40 is moved to the temperature control mechanism 80 of the analysis unit 70 while the nucleic acid analysis chip 20 is placed on the specimen-introducing part (S10). At the temperature control mechanism 80, the nucleic acid analysis chip 20 is inserted between the upper and lower heat plates 81 and 82. In addition, the nucleic acid analysis chip 20 is interposed between the upper and lower heat plates 81 and 82 as shown in FIG. 16. At this time, the protruding wall portion 28 comes into contact with the upper heat plate 81 and is elastically deformed, so that the protruding wall portion 28 comes into close contact with the upper heat plate 81. Accordingly, the injection port 26 and the outlet 27 (see FIG. 8A) are hermetically sealed by the protruding wall portion 28.

The upper and lower heat plates 81 and 82 are heated or cooled according to a preset temperature change. Accordingly, the temperature of the nucleic acid solution, which is stored in the reaction containers 22 of the nucleic acid analysis chip 20, is changed according to the preset temperature change. After that, nucleic acid amplifying reactions (PCR reactions) according to the specificities of the primer sets received in the container 22 are performed in each of the reaction containers 22 (S11).

When the nucleic acid amplifying reactions performed in the reaction containers 22 are completed, the reaction containers 22 are heated at a temperature of, for example, 99° C. for 10 minutes in order to deactivate DNA polymerase contained in the reaction containers 22 (S13). In the diffusion amplifying reactions, air bubbles are generated from the reagents and the like stored in the reaction containers 22 and may remain in the reaction containers 22. In this case, if necessary, an air bubble removing process (S12) for removing air bubbles generated in the reaction containers 22 during the PCR reactions may be performed before DNA polymerase is deactivated (S13) after the completion of the PCR reactions. Further, if necessary, an air bubble removing process (S14) may be performed after DNA polymerase is deactivated (S13). That is, any one of the air bubble removing processes (S12 and S14) may be performed one or two times.

The air bubble removing process is a process that rapidly cools the temperature of the reaction containers 22 of the nucleic acid analysis chip 20 to room temperature by the temperature control mechanism 80, moves the nucleic acid analysis chip 20 to the centrifugal liquid feed unit 60 from the analysis unit 70, and rotates the nucleic acid analysis chip 20 about the central axis O. Accordingly, the air bubbles remaining in the reaction containers 22 are extruded toward the flow passages 23 through centrifugal force that is applied to the liquid contained in the reaction containers 22 and the flow passages 23.

Since processes including, particularly, S14 or S4 to S13 can be automatically performed in the nucleic acid analyzer 1 according to this embodiment, it is possible to make timings for feeding a nucleic acid solution to each of the reaction containers 22 correspond with each other. Further, it is possible to minimize a time interval between the feed of the nucleic acid solution and the start of the PCR reactions (S11). As a result, it is possible to prevent a nucleic acid amplifying reaction from being unintentionally or artificially affected and to improve the accuracy of measurement results.

Figure 18:
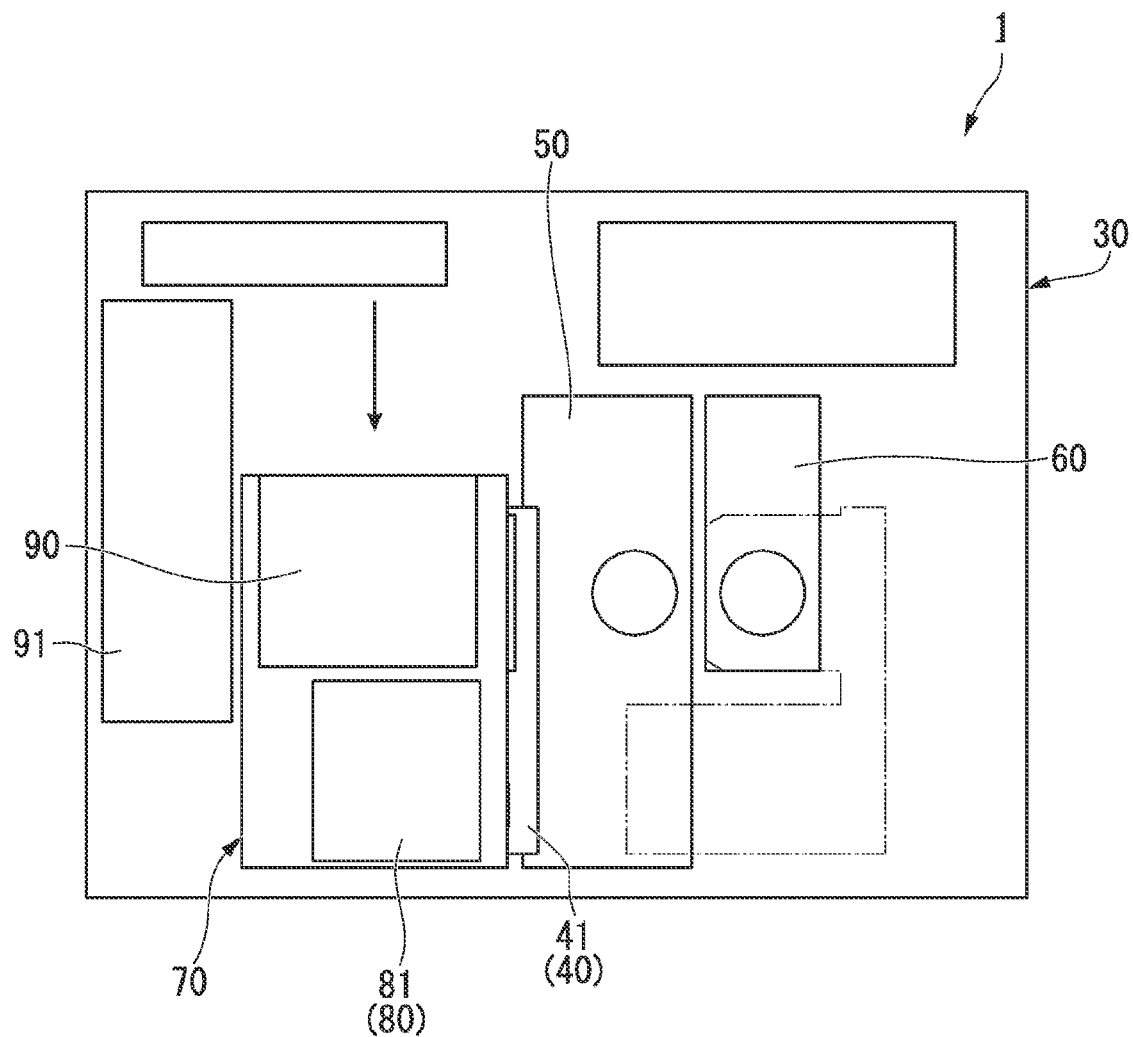
FIG. 18 is a view illustrating the operation of the nucleic acid analyzer at the time of the use of the nucleic acid analyzer.

Subsequently, SNP is measured by the invader (registered trademark) method in the reaction containers 22. First, as shown in FIG. 18, the analysis unit 70 is moved relative to the specimen-introducing part 40 so that the fluorescence measuring section 90 of the analysis unit 70 overlaps the nucleic acid analysis chip 20 (S15). Next, the temperature of the lower heat plate 82 is controlled so that the temperature of the liquid contained in the reaction container 22 is in the range of 60° C. to 70° C., preferably 63° C. Accordingly, an enzyme reaction is performed in the nucleic acid analysis chip 20 by the invader (registered trademark) method.

In the fluorescence measuring section 90, excitation light, which is generated by the optical part 91, is emitted to the reaction containers 22 through the optical fiber (not shown). Two kinds of excitation light having wavelengths of 480 nm and 545 nm are used in this embodiment in order to use measurement using the invader (registered trademark) method. A fluorescent material used in the invader (registered trademark) method is, specifically, FAM and RedmondRed. Since the reaction container 22 is transparent and can transmit light having a wavelength of 350 nm to 780 nm, excitation light reaches the inner portion of the reaction container 22 and reaches a fluorescent material released from the signal probe in the reaction container 22. In the reaction container 22, the fluorescence intensity is increased in proportion to the amount of the released fluorescent material. The fluorescence measuring section 90 sequentially measures the fluorescence intensity of each of FAM and RedmondRed in the reaction containers 22 in the circumferential direction of the nucleic acid analysis chip 20 (S16). Information measured by the fluorescence measuring section 90 is displayed on the terminal 2 shown in FIG. 1 (S17), so that a user can know which SNP is contained in nucleic acid.

As described above, according to the nucleic acid analyzer 1 of this embodiment, the purification of the nucleic acid using the nucleic acid purification kit 10 is performed by the purification treatment unit 50. Further, after a nucleic acid solution is fed to the respective reaction container 22 of the nucleic acid analysis chip 20 by the centrifugal liquid feed unit 60, the analysis of nucleic acid is performed by the analysis unit 70. As described above, the analysis of nucleic acid is performed while the respective units interlock with each other and the processes from the purification of nucleic acid to the analysis of nucleic acid can be automatically performed by the analyzer body 30. Accordingly, it is possible to easily perform an accurate gene test.

Further, among the processes for operating the nucleic acid analyzer 1, a process where a user's manual work is performed is a process that supplies a specimen (whole blood sample) to the sample well 11 of the nucleic acid purification kit 10 and places the nucleic acid purification kit 10 on the tray 41. This process does not require an accurate liquid operation, and all accurate liquid operations are performed by the analyzer body 30. Accordingly, even if a user is not skilled at liquid operations, the user can perform a gene test having high reproducibility.

Further, since the analysis unit 70 includes the temperature control mechanism 80, it is possible to immediately perform PCR reactions in the reaction containers 22 of the nucleic acid analysis chip 20 after the nucleic acid solution and the oil 127A are supplied to the nucleic acid analysis chip 20. For this reason, since a user's manual work is not needed, an operation is simple and it is possible to perform a gene test with accuracy through the increase of the specificities of PCR reactions.

Furthermore, since the analysis unit 70 includes the fluorescence measuring section 90, it is possible to measure the fluorescence of the fluorescent materials that are excited in the reaction containers 22 by excitation light.

Moreover, since the nucleic acid purification kit 10 includes the oil-removing unit 128, it is possible to remove the oil 127A, which adheres to the outer peripheral surface of the end 201A of the dispensing chip 201, by the wiping filter 129A of the oil-removing unit 128. Accordingly, when the end 201A of the dispensing chip 201 is inserted into the injection port 26 of the nucleic acid analysis chip 20, it is possible to suppress the adhering of the oil 127A to the outer surface of the nucleic acid analysis chip 20 around the injection port 26. As a result, when the nucleic acid analysis chip 20 is rotated by the centrifugal liquid feed unit 60, it is possible to suppress the scattering of the oil 127A that is caused through centrifugal force.

Further, since reagents and a filter unit, which are necessary to extract nucleic acid, are provided in the reagent cartridge 100 and integrated as a set, only an operation for adding a specimen to the sample well 110 and placing the reagent cartridge on the tray 41 of the specimen-introducing part 40 needs to be manually performed. Accordingly, it is possible to easily perform a gene test. Furthermore, since the waste liquid well 130 is integrally formed at the reagent cartridge 100, the reagent cartridge 100 merely needs to be removed and discarded from the tray 41 after the completion of a gene test. For this reason, since the treatment of waste liquid is simple, there is no concern that surroundings are contaminated with liquid remaining on a specimen and the like.

Moreover, since the reagent well portion 120 is sealed by the sealing film 104 provided on the reagent cartridge 100 and the reagents and the like can be sucked through the sealing film 104 by the end 201A of the dispensing chip 201, the reagent well portion 120 can be hermetically sealed until just before the reagents and the like are needed.

Further, a holding portion 160, which holds the extraction filter cartridge 150, is formed at the reagent cartridge 100. Accordingly, the extraction filter cartridge 150 does not fall down in the reagent cartridge 100 or the displacement of the extraction filter cartridge 150 does not occur in the reagent cartridge 100. Therefore, it is possible to automate the purification of nucleic acid through the stabilization of the posture of the extraction filter cartridge 150.

Furthermore, since the sealing film 103, which seals the opening of the reagent cartridge 100, is provided, it is possible to suppress the mixing of foreign materials to the extraction filter cartridge 150, the sample well 110, the collection well 140, and the like.

Moreover, since the claw portions 102, which fix the reagent cartridge to the tray 41, are formed at the reagent cartridge 100, the reagent cartridge 100 does not fall down or the reagent cartridge 100 is not displaced even though the specimen-introducing part 40 is moved in the analyzer body 30.

Further, since the flow passages 23 of the nucleic acid analysis chip 20 are formed closer to the central axis O than the reaction containers 22, it is possible to feed liquid to each of the reaction containers 22 from the flow passages 23 by rotating the nucleic acid analysis chip 20 about the central axis O.

Furthermore, since the injection port 26 is positioned on the central axis O, a centrifugal force applied to liquid, such as reagents or oil, adhering to the outer surface around the injection port 26 is small. Accordingly, when the nucleic acid analysis chip 20 is rotated about the central axis O by the centrifugal liquid feed unit 60, the scattering of the liquid, such as reagents or oil, is suppressed.

Moreover, since the protruding wall portion 28, which protrudes from the outer surface of the nucleic acid analysis chip body 21, is formed so as to surround the injection port 26, it is possible to hermetically seal the peripheral portion of the injection port 26 by making the protruding wall portion 28 come into contact with the upper heat plate 81 or the like. Accordingly, it is possible to prevent liquid and the like from being blown out of the injection port 26.

Further, since the protruding wall portion 28 has elasticity, it is possible to make the protruding wall portion 28 and the upper heat plate 81 come into close contact with each other.

Furthermore, since the flow restricting portions 25A are provided between the main flow passages 24 and the branch flow passages 25, it is possible to feed liquid to the reaction containers 22 through the branch flow passages 25 after all of the main flow passages 24 are filled with liquid.

Moreover, since chevron shapes 24C are formed at the main flow passages 24, the main flow passages 24 divided by the chevron shapes 24C can store the same amount of liquid. For this reason, it is possible to make the amount of liquid, which is fed to each of the reaction containers 22, uniform and to reduce an error of a biochemical reaction of each of the reaction containers 22.

Further, since the reaction container 22 has optical transparency, it is possible to perform optical measurement of the inside of the reaction container 22 from the outside of the nucleic acid analysis chip 20.

Furthermore, since the nucleic acid analysis chip 20 includes the chip body 21 where the reaction containers 22 and the flow passages 23 are formed and the lid body 29 that is attached to the chip body 21, it is easy to dispose different probes, primers, and reagents in each of the reaction containers 22. Moreover, after the lid body 29 is attached to the chip body 21, biochemical reaction can be preferably performed in each of the reaction containers 22 as independent reaction spaces.

Further, since the lid body 29 is made of a metal material, it is possible to rapidly heat and cool each of the reaction containers 22.

An example of gene analysis, which uses the nucleic acid analyzer 1 according to this embodiment, will be described below.

Examples of gene analysis, which uses the nucleic acid analyzer 1, may include the detection of K-ras germline mutation and the detection of germline mutation.

A K-ras gene is known as a cancer gene derived from a virus, and is a gene that codes a type of G protein having GTPase activity. It is considered that when a point mutation occurs at the K-ras gene, GTPase activity is reduced, so that the change of a cell to a cancer is caused.

Germline mutation is an individual characteristic mutation that occurs while a reproductive cell has mutation, and there is the same mutation in all individual cells. It is considered that it is possible to estimate differences and the like of, for example, drug susceptibility by analyzing germline mutation.

(Detection of K-Ras Germline Mutation)

First, an example where the nucleic acid analyzer 1 according to this embodiment is used to detect a K-ras germline mutation will be described.

Probes, which correspond to a wild type of the K-ras gene and thirteen mutation types, and salt and the above-mentioned enzyme used to amplify nucleic acid are previously stored in each of the reaction containers 22. In this case, since fourteen types of probes are provided, fourteen reaction containers 22 are used at the nucleic acid analysis chip 20.

A user supplies a specimen, which is suspected as pancreatic cancer, bowel cancer, or the like, to the sample well 110 of the reagent cartridge 100 of the nucleic acid purification kit 10, and performs the extraction of nucleic acid, the amplifying reaction of a gene in nucleic acid, and the measurement of fluorescence intensity by operating the nucleic acid analyzer 1 as described above. Accordingly, it is possible to determine whether the specimen has a K-ras germline mutation or not and which mutation type among K-ras mutation types corresponds to the K-ras germline mutation.

(Detection of Germline Mutation)

Since germline mutation is a mutation common to all individual cells, it is possible to detect a germline mutation by using, for example, a whole blood sample or the like. Specifically, it is possible to detect a germline mutation by specifying the SNP of the specimen. For example, a PCR-PHFA (PCR-Preferential Homoduplex Formation Assay) method is known as a method of specifying SNP.

Since it is possible to make the amount of liquid, which is fed to each of the reaction containers 22, uniform by performing a PCR-PHFA method with the nucleic acid analysis chip 20 of this embodiment, measurement errors between the plurality of reaction containers 22 are reduced. Accordingly, it is possible to improve detection accuracy when the presence or absence of SNP is detected through differences in fluorescence intensity in the plurality of reaction containers 22.

Further, the invader (registered trademark) method, a Taqman PCR method, and the like are known as methods of specifying SNP, but the nucleic acid analyzer 1 according to this embodiment may also be preferably used in these methods.

The embodiment of the invention has been described in detail above with reference to the drawings. However, the specific structure is not limited to this embodiment, and a change in design and the like without departing from the scope of the invention are included in the invention. Moreover, the components shown in the above-mentioned embodiment and modifications may be appropriately combined.

For example, the analysis unit 70 includes the temperature control mechanism 80 and the fluorescence measuring section 90, but it is possible to more easily perform an accurate gene test even if the analysis unit 70 does not include the temperature control mechanism 80 and the fluorescence measuring section 90.

Further, it is preferable that the nucleic acid purification kit 10 include a dispensing chip rack 200 in which oil 127A and at least an oil-dispensing chip 201 dispensing oil are stored and an oil-removing unit 128 removing surplus oil adhering to the outer surface of the end portion of the oil-dispensing chip 201.

Furthermore, it is preferable that the nucleic acid purification kit 10 include a box-shaped reagent cartridge 100 and a reagent-dispensing chip 201 and the reagent cartridge 100 include a sample well 110, an oil well 127, reagent wells 121, 122, 123, 124, 125, and 126, a waste liquid well 130, and an extraction filter cartridge 150.

In addition, the reagent cartridge 100 is provided with a sealing film (opening portion sealing film) 104 that is formed so as to be capable of being penetrated by the end of the reagent-dispensing chip 201 or the oil-dispensing chip 201, but is not limited thereto. The holding portion 160 in which the extraction filter cartridge 150 is received is formed integrally with the reagent cartridge 100, but is not limited thereto.

Further, the claw portions 102 have been formed as the positioning mechanism that positions the reagent cartridge 100 on the specimen-introducing part 40, but is not limited thereto.

Furthermore, the nucleic acid analysis chip 20 has included the flow passages 23 and the injection port 26, but is not limited thereto. The nucleic acid analysis chip 20 has included the chip body 21 and the lid body 29, but is not limited thereto. It is preferable that at least one of the chip body 21 and the lid body 29 have optical transparency.

In addition, the protruding wall portion 28, which protrudes from the outer surface of the chip body 21 so as to surround the injection port 26 and the outlet 27, has been described, but is not limited thereto.

Further, the protruding wall portion 28 has elasticity, but is not limited thereto. Furthermore, the flow passage 23 includes the main flow passage 24 and the branch flow passage 25, but is not limited thereto. Moreover, the main flow passage 24 has a chevron shape, but is not limited thereto.

REFERENCE SIGNS LIST

1: nucleic acid analyzer
2: terminal
10: nucleic acid purification kit
20: nucleic acid analysis chip
21: chip body
22: reaction container
23: flow passage
24: main flow passage
24A: one end 24B: the other end
24C: chevron shape
24D: apex
25: branch flow passage
25A: flow restricting portion
26: injection port
27: outlet
28: protruding wall portion
29: lid body
30: analyzer body
31: housing
40: specimen-introducing part
41: tray
42: analysis chip holder
43: engagement portion
50: purification treatment unit
51: robot hand
52: dispensing section
53: pressurizing section
55: transport unit (transport part)
60: centrifugal liquid feed unit
70: analysis unit
80: temperature control mechanism
81: upper heat plate
81A: convex region 81A
82: lower heat plate
90: fluorescence measuring section
91: optical part
100: reagent cartridge
101: body
102: claw portion (positioning mechanism)
103: sealing film
104: sealing film
110: sample well (specimen storage portion)
120: reagent well portion
121, 122, 123, 124, 125, 126: reagent well (reagent storage portion)
121A, 122A: solution
123A, 124A: washing solution
125A: eluate
126A: diluted solution
127: oil well (oil storage portion)
127A: oil
128: oil-removing unit
129: wiper
129A: wiping filter
129B, 129D: support part
129C: slit (through-hole)
129E: slit (true circular shape)
129F: slit (circular shape with protruding portions)
130: waste liquid well (waste liquid storage portion)
140: collection well
150: extraction filter cartridge
151: body (substantially cylindrical shape)
151A: upper end
151B: lower end
151C: discharge port (nozzle shape)
152: extraction filter unit
152A: adsorption filter
152B: support member
160: holding portion
200: dispensing chip rack
201: dispensing chip (oil-dispensing chip, reagent-dispensing chip)
201A: end
O: central axis (rotation axis)

The invention claimed is:
1. A nucleic acid analyzer comprising:
a nucleic acid purification kit that yields a nucleic acid solution by isolating and purifying nucleic acid from a specimen;
a nucleic acid analysis chip that has a rotation axis positioned at a center thereof, includes a plurality of reaction containers at an outer portion than the rotation axis in a radial direction, and feeds the nucleic acid purified by the nucleic acid purification kit, to the reaction containers through centrifugal force around the rotation axis, wherein
the nucleic acid analysis chip includes a main flow passage and a plurality of branch flow passages,
the main flow passage is arranged in a circumferential direction around the rotation axis and has a plurality of first turning portions and a plurality of second turning portions, each of the first turning portions being positioned outward in the radial direction, each of the second turning portions being positioned inward in the radial direction relative to the first turning portions, and each of the second turning portions being connected to adjacent first turning portions,
the plurality of first turning portions are in fluid communication with the plurality of reaction containers respectively, by the plurality of branch flow passages respectively, and
at least at each connected of portions of the plurality of branch flow passages and the plurality of first turning portions, the branch flow passage is narrower than the first turning portions;
a specimen-introducing part on which the nucleic acid purification kit is placed;
an analysis chip holder that is provided at the specimen-introducing part and supports the nucleic acid analysis chip;
a purification treatment unit that injects the nucleic acid solution containing the nucleic acid into the nucleic acid analysis chip;
a centrifugal liquid feed unit that feeds the nucleic acid solution to each of the reaction containers by rotating the nucleic acid analysis chip about the rotation axis;
an analysis unit that analyzes reaction products in the reaction containers; and
transport part for relatively transporting the specimen-introducing part to each of the purification treatment unit, the centrifugal liquid feed unit, and the analysis unit.

2. The nucleic acid analyzer according to claim 1, wherein the analysis unit includes a temperature control mechanism that comes into contact with an outer surface of the reaction containers of the nucleic acid analysis chip and heats or cools the reaction containers so that a temperature of the reaction containers follows a predetermined temperature change.

3. The nucleic acid analyzer according to claim 2, wherein the analysis unit includes a fluorescence measuring section that emits excitation light having a predetermined wavelength that excites a fluorescent material in the reaction containers of the nucleic acid analysis chip, and measures an intensity of fluorescence emitted from the fluorescent material.

4. The nucleic acid analyzer according to claim 1, wherein the nucleic acid purification kit includes: oil that is supplied to the nucleic acid analysis chip; a dispensing tip-receiver in which at least an oil-dispensing tip that dispenses the oil is stored, and an oil-removing unit that removes surplus oil adhering to an outer surface of an end portion of the oil-dispensing tip.

5. The nucleic acid analyzer according to claim 4,
wherein the oil-removing unit includes a lipophilic wiper that comes into contact with the outer surface of the oil-dispensing tip when an end of the oil-dispensing tip is inserted.

6. The nucleic acid analyzer according to claim 4,
wherein the nucleic acid purification kit includes a box-shaped reagent cartridge, and a plurality of reagent-dispensing tips that are stored in the dispensing tip-receiver, and
the reagent cartridge includes: a specimen storage portion that stores the specimen; an oil storage portion that stores the oil; a reagent storage portion that stores a liquid reagent used for the isolation and purification of the nucleic acid; a waste liquid storage portion that stores waste liquid generated during the isolation and the purification; and an extraction filter cartridge that purifies the nucleic acid of the specimen.

7. The nucleic acid analyzer according to claim 6,
wherein the reagent cartridge is provided with an opening portion sealing film that seals each of the oil storage portion and the reagent storage portion and is formed penetrable by an end of the reagent-dispensing tip or the oil-dispensing tip.

8. The nucleic acid analyzer according to claim 6,
wherein the reagent cartridge includes a holding portion that detachably holds the extraction filter cartridge.

9. The nucleic acid analyzer according to claim 8,
wherein the holding portion includes an absorbent body that absorbs liquid passing through the extraction filter cartridge.

10. The nucleic acid analyzer according to claim 6, further comprising:
a cartridge-sealing film that seals an opening of the reagent cartridge.

11. The nucleic acid analyzer according to claim 6,
wherein the reagent cartridge includes a positioning mechanism that positions the reagent cartridge on the specimen-introducing part.

12. The nucleic acid analyzer according to claim 1,
wherein the nucleic acid analysis chip includes an injection port that is opened and formed closer to the rotation axis than the main flow passage and that is in fluid communication with the main flow passage.

13. The nucleic acid analyzer according to claim 12,
wherein the injection port is opened coaxially with the rotation axis,
the nucleic acid analyzer further comprising:
a protruding wall portion that protrudes from the outer surface of the nucleic acid analysis chip so as to surround the injection port.

14. The nucleic acid analyzer according to claim 13,
wherein the protruding wall portion has elasticity.

15. The nucleic acid analyzer according to claim 12,
wherein the plurality of branch flow passages are formed so as to be thinner than the main flow passage.

16. The nucleic acid analyzer according to claim 12,
wherein the main flow passage has a plurality of chevron-shaped protruding portions, each protruding inwardly in a radial direction.

17. The nucleic acid analyzer according to claim 12,
wherein at least a part of the reaction container has optical transparency.

18. The nucleic acid analyzer according to claim 12,
wherein the nucleic acid analysis chip includes a chip body where concave portions forming the reaction containers and the main flow passage and the plurality of branch flow passages are formed on one surface; and a lid body that is attached to the one surface of the chip body so as to lid the concave portions.

19. The nucleic acid analyzer according to claim 18,
wherein at least one of the chip body and the lid body has optical transparency.

20. The nucleic acid analyzer according to claim 18,
wherein the chip body is made of a resin material having optical transparency, and the lid body is made of a metal material.

21. The nucleic acid analyzer according to claim 2, wherein the nucleic acid purification kit includes: oil that is supplied to the nucleic acid analysis chip; a dispensing tip-receiver in which at least an oil-dispensing tip that dispenses the oil is stored, and an oil-removing unit that removes surplus oil adhering to an outer surface of an end portion of the oil-dispensing tip.

22. The nucleic acid analyzer according to claim 3, wherein the nucleic acid purification kit includes: oil that is supplied to the nucleic acid analysis chip; a dispensing tip-receiver in which at least an oil-dispensing tip that dispenses the oil is stored, and an oil-removing unit that removes surplus oil adhering to an outer surface of an end portion of the oil-dispensing tip.

23. The nucleic acid analyzer according to claim 21,
wherein the oil-removing unit includes a lipophilic wiper that comes into contact with the outer surface of the oil-dispensing tip when an end of the oil-dispensing tip is inserted.

24. The nucleic acid analyzer according to claim 22,
wherein the oil-removing unit includes a lipophilic wiper that comes into contact with the outer surface of the oil-dispensing tip when an end of the oil-dispensing tip is inserted.

25. The nucleic acid analyzer according to claim 21,
wherein the nucleic acid purification kit includes a box-shaped reagent cartridge, and a plurality of reagent-dispensing tip that are stored in the dispensing tip-receiver, and
the reagent cartridge includes: a specimen storage portion that stores the specimen; an oil storage portion that stores the oil; a reagent storage portion that stores a liquid reagent used for the isolation and purification of the nucleic acid; a waste liquid storage portion that stores waste liquid generated during the isolation and the purification; and an extraction filter cartridge that purifies the nucleic acid of the specimen.

26. The nucleic acid analyzer according to claim 22,
wherein the nucleic acid purification kit includes a box-shaped reagent cartridge, and a plurality of reagent-dispensing tips that are stored in the dispensing tip-receiver, and
the reagent cartridge includes: a specimen storage portion that stores the specimen; an oil storage portion that stores the oil; a reagent storage portion that stores a liquid reagent used for the isolation and purification of the nucleic acid; a waste liquid storage portion that stores waste liquid generated during the isolation and the purification; and an extraction filter cartridge that purifies the nucleic acid of the specimen.

27. The nucleic acid analyzer according to claim 25,
wherein the reagent cartridge is provided with an opening portion sealing film that seals each of the oil storage portion and the reagent storage portion and is formed penetrable by an end of the reagent-dispensing tip or the oil-dispensing tip.

28. The nucleic acid analyzer according to claim 26,
wherein the reagent cartridge is provided with an opening portion sealing film that seals each of the oil storage portion and the reagent storage portion and is formed penetrable by an end of the reagent-dispensing tip or the oil-dispensing tip.

29. The nucleic acid analyzer according to claim 25,
wherein the reagent cartridge includes a holding portion that detachably holds the extraction filter cartridge.

30. The nucleic acid analyzer according to claim 26,
wherein the reagent cartridge includes a holding portion that detachably holds the extraction filter cartridge.

31. The nucleic acid analyzer according to claim 29,
wherein the holding portion includes an absorbent body that absorbs liquid passing through the extraction filter cartridge.

32. The nucleic acid analyzer according to claim 30,
wherein the holding portion includes an absorbent body that absorbs liquid passing through the extraction filter cartridge.

33. The nucleic acid analyzer according to claim 25, further comprising:
a cartridge-sealing film that seals an opening of the reagent cartridge.

34. The nucleic acid analyzer according to claim 26, further comprising:
a cartridge-sealing film that seals an opening of the reagent cartridge.

35. The nucleic acid analyzer according to claim 25,
wherein the reagent cartridge includes a positioning mechanism that positions the reagent cartridge on the specimen-introducing part.

36. The nucleic acid analyzer according to claim 26,
wherein the reagent cartridge includes a positioning mechanism that positions the reagent cartridge on the specimen-introducing part.

* * * * *